US010117580B1

(12) United States Patent
Puryear et al.

(10) Patent No.: US 10,117,580 B1
(45) Date of Patent: Nov. 6, 2018

(54) SYSTEMS, DEVICES AND METHODS THAT AFFECT NEURAL TISSUE THROUGH THE DELIVERY OF A PULSED RADIO FREQUENCY SIGNAL GENERATED BY AN IMPLANTABLE MEDICAL DEVICE

(71) Applicant: SynerFuse, Inc., Minneapolis, MN (US)

(72) Inventors: Harry Puryear, Shoreview, MN (US); Timothy J. Cox, Leonard, TX (US); Serafin Y. Samson, Maple Grove, MN (US); Nazmi Peyman, Glen Allen, VA (US); Omid Souresrafil, Maple Grove, MN (US); Gregory F. Molnar, Blaine, MN (US)

(73) Assignee: SynerFuse, Inc., Minneapolis, MN (US)

( * ) Notice: Subject to any disclaimer, the term of this patent is extended or adjusted under 35 U.S.C. 154(b) by 0 days.

(21) Appl. No.: 15/727,554

(22) Filed: Oct. 6, 2017

Related U.S. Application Data

(60) Provisional application No. 62/502,604, filed on May 6, 2017, provisional application No. 62/531,129, filed on Jul. 11, 2017.

(51) Int. Cl.
*A61N 1/06* (2006.01)
*A61N 1/36* (2006.01)
(Continued)

(52) U.S. Cl.
CPC .............. *A61B 5/0031* (2013.01); *A61N 1/06* (2013.01); *A61N 1/40* (2013.01); *A61N 1/0551* (2013.01);
(Continued)

(58) Field of Classification Search
CPC combination set(s) only.
See application file for complete search history.

(56) References Cited

U.S. PATENT DOCUMENTS

| 5,733,313 | A | 3/1998 | Barreras et al. |
| 6,227,204 | B1 * | 5/2001 | Baumann ................ H02J 7/025 |
| | | | 128/899 |

(Continued)

OTHER PUBLICATIONS

Erdine et al., Ultrastructural Changes in Axons Following Exposure to Pulsed Radiofrequency Fields, World Institute of Pain, Pain Practice, vol. 9, Issue 6, 2009, pp. 407-417.
(Continued)

*Primary Examiner* — Joseph Stoklosa
*Assistant Examiner* — Adam Avigan
(74) *Attorney, Agent, or Firm* — Loza & Loza, LLP; David S. Sarisky

(57) ABSTRACT

Radio frequency (RF) energy is transmitted through the application of a RF signal to an external RF energy interface, where the RF signal oscillates at a frequency in an energy transmission band. The transmitted RF energy is received at an implanted medical device, and energy derived from the received RF energy is stored in a direct current (DC) energy storage component of the device. A therapeutic output signal is generated from the stored energy and delivered by the implantable medical device to a patient through one or more electrodes. The therapeutic output signal is configurable to provide either one of RF stimulation therapy and RF ablation therapy, and comprises pulses of an RF signal oscillating at a frequency in a therapy band that is greater than the energy transmission band.

27 Claims, 22 Drawing Sheets

(51) Int. Cl.
*A61N 1/05* (2006.01)
*A61B 5/00* (2006.01)
*A61N 1/40* (2006.01)

(52) U.S. Cl.
CPC ........ *A61N 1/3605* (2013.01); *A61N 1/36057* (2013.01); *A61N 1/36062* (2017.08)

(56) References Cited

U.S. PATENT DOCUMENTS

| | | | |
|---|---|---|---|
| 6,248,126 B1 | 6/2001 | Lesser et al. | |
| 6,364,899 B1 | 4/2002 | Dobak | |
| 6,418,345 B1 | 7/2002 | Tepper et al. | |
| 6,699,268 B2 | 3/2004 | Kordis et al. | |
| 7,306,621 B1 | 12/2007 | Halla et al. | |
| 7,500,985 B2 | 3/2009 | Saadat | |
| 8,165,682 B2 | 4/2012 | Gopalsami et al. | |
| 8,202,308 B2 | 6/2012 | Smyth | |
| 8,275,461 B2 | 9/2012 | Birkill et al. | |
| 8,414,509 B2 | 4/2013 | Diederich et al. | |
| 8,428,728 B2 | 4/2013 | Sachs | |
| 8,473,067 B2 | 6/2013 | Hastings et al. | |
| 8,523,930 B2 | 9/2013 | Saunders et al. | |
| 8,591,562 B2 | 11/2013 | D'Ambrosio et al. | |
| 8,606,358 B2 | 12/2013 | Sachs | |
| 8,874,230 B2 | 10/2014 | Niver et al. | |
| 8,911,486 B1 | 12/2014 | Drnek et al. | |
| 8,986,296 B2 | 3/2015 | Peyman | |
| RE45,718 E * | 10/2015 | Kilgore | A61N 1/36071 |
| 9,198,735 B2 | 12/2015 | Taghizadeh | |
| 9,248,278 B2 | 2/2016 | Crosby et al. | |
| 9,295,517 B2 | 3/2016 | Peymen et al. | |
| 9,409,030 B2 | 8/2016 | Perryman et al. | |
| 9,474,573 B2 | 10/2016 | Leung et al. | |
| 9,511,228 B2 * | 12/2016 | Amurthur | A61N 1/36117 |
| 9,585,602 B1 | 3/2017 | Navarro et al. | |
| 9,623,238 B2 | 4/2017 | Sharma et al. | |
| 9,630,011 B2 | 4/2017 | Lipani | |
| 2007/0135875 A1* | 6/2007 | Demarais | A61F 7/123 607/96 |
| 2007/0203521 A1* | 8/2007 | Dobak | A61N 1/36007 607/2 |
| 2011/0137380 A1 | 6/2011 | Tseng et al. | |
| 2011/0224665 A1* | 9/2011 | Crosby | A61B 18/1492 606/33 |
| 2013/0274735 A1 | 10/2013 | Hastings et al. | |
| 2013/0296977 A1* | 11/2013 | Chiu | A61B 18/18 607/89 |
| 2013/0317585 A1* | 11/2013 | Barker | A61N 1/0558 607/117 |
| 2014/0046398 A1 | 2/2014 | Sachs et al. | |
| 2014/0249603 A1* | 9/2014 | Yan | A61N 1/3787 607/61 |
| 2015/0025613 A1* | 1/2015 | Nyberg, II | H01Q 1/273 607/137 |
| 2015/0048790 A1 | 2/2015 | Rudser et al. | |
| 2016/0128573 A1 | 5/2016 | Wilder et al. | |
| 2017/0143984 A1 | 5/2017 | Otten et al. | |
| 2017/0216602 A1 | 8/2017 | Waataja et al. | |

OTHER PUBLICATIONS

Higuchi et al., Exposure of the Dorsal Root Ganglion in Rats to Pulsed Radiofrequency Currents Activates Dorsal Horn Lamina I and II Neurons, Experimental Studies, Neurosurgery, vol. 50, No. 4, Apr. 2002, pp. 850-856.

Huang et al., Rapid and Delayed Effects of Pulsed Radiofrequency on Neuropathic Pain: Electrophysiological, Molecular, and Behavioral Evidence Supporting Long-Term Depression, Pain Physician Journal, Pain Physician: Feb. 20, 2017, pp. 266-E283.

* cited by examiner transmitted by RF generator/controller (60KHz)

received by RF Module (60Khz), charges energy storage component energy obtained from the energy storage component RF heat signal generated and output by RF module (450KHz)

SYSTEMS, DEVICES AND METHODS THAT AFFECT NEURAL TISSUE THROUGH THE DELIVERY OF A PULSED RADIO FREQUENCY SIGNAL GENERATED BY AN IMPLANTABLE MEDICAL DEVICE

CROSS-REFERENCE TO RELATED APPLICATION(S)

This application claims the benefit of U.S. Provisional Application Ser. No. 62/502,604, entitled "Systems and Methods for Generating Therapeutic Modes of Energy at Targeted Areas of a Patient's Body" and filed on May 6, 2017, and U.S. Provisional Application Ser. No. 62/531,129 entitled "Smart Implantable Spinal Stabilization/Cage System Capable of Delivering Radiofrequency Energy to the Spine Via Implantable Transcutaneous Rechargeable Pulse Generator and Spinal Stimulation Lead System" and filed on Jul. 11, 2017, each of which is expressly incorporated by reference herein in its entirety.

BACKGROUND

Field

The present disclosure relates generally to systems, devices, and methods related to delivery of therapy for treatment of pain, and more particularly, to systems, devices, and methods that affect neural tissue through the delivery of a pulsed radio frequency (RF) signal generated by an implantable medical device. The present disclosure also relates generally to systems, devices, and methods related to monitoring the condition of a patient having an orthopedic implant device, and more particularly, to systems, devices, and methods that collect and assess information directed to the mechanical integrity of an orthopedic implant device and the activity of the patient as may be affected by the implant device.

Background

The number of people having spinal conditions that result in discomfort and pain is increasing rapidly, mainly due to sedentary lifestyle and other postural and physical habits. Some spinal conditions of this nature may be treated by non-surgical procedures, including for example, exercise regimens to strengthen core abdominal muscles. Sometimes, however, a surgical procedure is necessary. Conditions requiring surgery include, for example, disc slip, degenerated disc, spinal tumor, degenerated spine, spinal stenosis, fracture of the vertebrae, posterior rami syndrome and spinal instability such as scoliosis (sideways curvature of the spine) and kyphosis (an abnormally excessive convex curvature of the spine in the cervical, thoracic and sacral regions).

These surgical procedures may involve fusion, where one or more vertebrae are surgically fused together using bone grafting, to prevent relative motion among the fused vertebrae. Implant devices utilizing specially designed spinal instrumentation are also often used in these surgical procedures to facilitate fusion, correct deformities, and stabilize and strengthen the spine.

Example implant devices include rod and screw sets, interspinous process devices, and interbody fusion devices. A rod and screw set includes a pair of pedicle screws that are fixed in the pedicles of the spinal vertebra to provide anchorage points for a rod that spans between the screws. The rods, which are typically formed of titanium or stainless steel, attach to the screws and make the affected segments of the spine immobile, for the purpose of accurately aligning the spine, which promotes fusion and removes deformities. While the rods are strong, they have some flexibility so that the surgeon can shape the rod to match the contours of the spine.

Interspinous process devices are used to treat lumbar spinal degenerative disease that reduces the lumen of the spinal canal for the passage of the nerves, leading to compression of nerve roots. Indications for the implantation of an interspinous process device are spinal stenosis and neurogenic claudication. The primary aim of interspinous process devices is to limit lumbar extension in the area of stenosis and to enlarge the spinal canal and open the intervertebral foramina to thereby achieve indirect decompression of the nerve roots in their passage through the foramina. More recent interspinous process devices have been designed to provide non-pedicle supplemental spine fixation to achieve supplemental fusion. These more recent designs for supplemental fusion are referred to as interspinous process fusion devices.

Interbody fusion devices are used to restore lost disc height resulting from a collapsed disc and to relieve pressure on nerve roots. One type of interbody fusion device, referred to as a "cage" is a small hollow device with perforated walls that is configured to be placed between two vertebrae, in place of a disc. A bone graft may be packed into the cage to promote bone growth between the adjacent vertebrae. Another type of interbody fusion device is configured to be placed within the annulus of a disc. This type of interbody fusion device comprises a set of modules that are individually placed within the annulus adjacent each other in an arrangement that substantially fills the interior of the annulus.

Pain is a distressing sensation conveyed from the affected part of the body to the spinal column and then to the brain by specialized nerves termed sensory or efferent nerves. The body possesses receptors or free nerve endings that detect sensations that can range from pleasant to annoying to distressing and are termed stimuli. Stimuli are transmitted through the nerve axon in the form of action potentials, a form of electrical energy created by the transfer of ions across the axon membrane. The sensory nerves are a branching network that radiate from nerves branching from the spinal cord through the vertebral foramen and thence on to parts of the body associated with that particular level of the spinal column. In the region of the vertebral foramen is a specialized mass of nervous tissue called the dorsal root ganglion (DRG). The cells of the DRG convert the action potentials transmitting sensation into a different mechanism for transmission along the spinal column to the brain. Nerve cells are thus classified as pre-ganglionic or post-ganglionic. Also, the action potential of sensory nerves can be as short as 1 millisecond, which translates to a frequency at 1 KHz.

The spinal conditions cited above generate pain by several modes. The first is that damaged discs and vertebral structures generate pain via sensory nerves. Another mode is termed spinal stenosis where the nerves passing through the vertebral foramen are compressed, generating pain that appears to come from another part of the body. Finally, the spine stabilization methods and means can generate pain.

The use of electrical energy to stimulate or modulate nerves is based on modulating the action potentials of the nerve axon. Several medical devices have been created to apply electrical energy to the nerves of the body in attempts to provide pain relief by interrupting the transmission of sensation through the nerve. The electrical energy can be applied as direct current (DC) or alternating current (AC). DC applications have limitations such as causing pain and even burns. AC applications have used frequencies from less than 1 Hz up to 50 KHz to disrupt or modulate nerve transmission. There are various claims for the selection of one frequency over another. Historically, nerve stimulation can be achieved at 10 Hz and blocked at 100 Hz. Higher frequencies up to 50 KHz have been investigated and found to have some effect.

AC energy in the radiofrequency band has been used to destroy nerve cells. Historically the frequency band utilized has been limited to 100-500 KHz. AC current is continuously applied to the targeted tissue and the oscillating current generates heat resulting in elevated temperature that cause nerve cell necrosis. This mode of therapy has been used to destroy many types of body cells, notably cardiac and cancer. Another mode of RF tissue destruction is pulsed RF (PRF). PRF may be applied to the targeted tissues, for example, in pulses of 20-50 μsec at the rate of 2-8 Hz with an amplitude of 50-100V. This mode of application, however, does not generate sufficient heat to cause cell necrosis but the PRF interferes with the cellular mechanisms for transporting ions across cell membranes.

In current medical practice, pain management in the anatomical region of the spinal column is conducted with chronic implanted spinal stimulators that deliver neurostimulation, typically in the form of charge-balanced, biphasic direct current (DC) pulses delivered at a frequency in the range of 10 Hz-10 KHz. Spinal stimulation therapy is applied to the spinal column and more recently to the DRG. Implanted spinal stimulators are battery powered and limited to neuromodulation stimulation in the form of DC pulses that preserves battery life.

Pain management in the region of the spinal column may also involve acute procedures such as RF and PRF ablation. RF and PRF therapies have been limited to means whereby a direct electrical connection is made between an external RF generator and a probe within the body in contact with the targeted tissue. The probe is inserted percutaneously to the targeted tissue and withdrawn after treatment. This method is necessitated by the energy requirements of the therapy.

It is desirable to provide means and methods to disrupt pain signals in the region local to the spinal column with an implanted device that can deliver both neuromodulation therapies and neuro-necrotic therapies. The therapies would be applied selectively. Furthermore, the device would be powered by an external source using wireless power transfer. Included in the device function would be sensors for monitoring the health of the spinal area and telemetry for reporting the status of one or more of patient activity, therapy delivery, and mechanical integrity of the spinal area, to an external module. The concepts disclosed below address these needs and others.

SUMMARY

The various embodiments herein provide systems, device, and methods directed to the delivery of RF therapy by an implantable medical device to relieve back pain associated with orthopedic implant devices and/or to the monitoring of the mechanical integrity of such implant devices. The various embodiments herein also provide for structural association or integration of the implantable medical device with orthopedic implant devices.

In one embodiment, a pain management system includes an external device and an implantable medical device. The external device is configured to transmit radio frequency (RF) energy through the application of a RF signal to an external RF energy interface, where the RF signal oscillates at a frequency in an energy transmission band. The implantable medical device includes one or more electrodes configured to be implanted in, on, or adjacent a target area of nerves, an implantable RF energy interface configured to receive energy from the external RF energy interface over a wireless energy link, and an energy storage component configured to store the energy. The implantable medical device also includes a RF therapy controller coupled to the energy storage component and the one or more electrodes. The RF therapy controller is configured to: 1) generate a therapeutic output signal from the stored energy, the therapeutic output signal configurable to provide either one of RF stimulation therapy and RF ablation therapy, and comprising pulses of an RF signal oscillating at a frequency in a therapy band that is greater than the energy transmission band, and 2) deliver the therapeutic output signal to one or more of the plurality of electrodes.

In another embodiment, an implantable medical device configured for chronic implant includes one or more electrodes configured to be implanted in, on, or adjacent a target area of nerves, an RF energy interface configured to receive energy from an external RF energy interface over a wireless energy link, and an energy storage component coupled to the RF energy interface through charging circuitry and configured to store the energy. The implantable medical device further includes a RF therapy controller coupled to the energy storage component and the one or more electrodes. The RF therapy controller is configured to: 1) generate a therapeutic output signal from the stored energy, the therapeutic output signal comprising pulses of an RF signal oscillating at a frequency in a therapy band, and 2) deliver the therapeutic output signal to one or more of the plurality of electrodes.

In another embodiment, a method of delivering RF therapy to a patient includes transmitting radio frequency (RF) energy through the application of a RF signal to an external RF energy interface, where the RF signal oscillates at a frequency in an energy transmission band. The method also includes receiving the RF energy at an implanted medical device, and storing energy derived from the received RF energy in a direct current (DC) energy storage component. The method further includes generating a therapeutic output signal from the stored energy and delivering the therapeutic output signal to one or more of the electrodes. The therapeutic output signal is configurable to provide either one of RF stimulation therapy and RF ablation therapy, and comprises pulses of an RF signal oscillating at a frequency in a therapy band that is greater than the energy transmission band.

In yet another embodiment, an implantable medical device configured for chronic implant includes one or more electrodes configured to be implanted in, on, or adjacent a target area of nerves, and an RF energy interface configured to receive energy from an external RF energy interface over a wireless energy link. The device also includes a housing having therein, an energy storage component coupled to the RF energy interface through charging circuitry and configured to store the energy. A RF therapy controller also within the housing is coupled to the energy storage component and the one or more electrodes. The RF therapy controller is configured to: 1) generate a therapeutic output signal from the stored energy, the therapeutic output signal comprising pulses of an RF signal oscillating at a frequency in a therapy band, and 2) deliver the therapeutic output signal to one or more of the plurality of electrodes. The housing is configured to be associated with an orthopedic implanted device comprising a piece of implant hardware.

In another embodiment, an orthopedic implant device configured for chronic implant in a patient includes at least one implant structure, e.g., a rod or a pedicle screw, configured to be associated with a boney structure. One or more components of an implantable medical device are integrated with the implant structure. The implantable medical device may be configured to generate a therapeutic output signal in a form of a pulsed a radio frequency (RF) signal, and deliver the signal to neural tissue. Alternatively, the implantable medical device may be configured to collect information related to the mechanical integrity of the orthopedic implant device.

In yet another embodiment, an implantable medical device configured for chronic implant in a patient includes a housing. At least one of a radio frequency (RF) module configured to generate a therapeutic output signal in a form of a pulsed a RF signal, and deliver the signal to neural tissue of the patient, and a health information module configured to collect information directed to a mechanical integrity of an orthopedic implant device and an activity of the patient, is located within the housing. The housing is configured to be associated with an orthopedic implanted device comprising a piece of implant hardware.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, devices, and methods will now be presented in the detailed description by way of example, and not by way of limitation, with reference to the accompanying drawings, wherein.

DETAILED DESCRIPTION

Figure 1A:
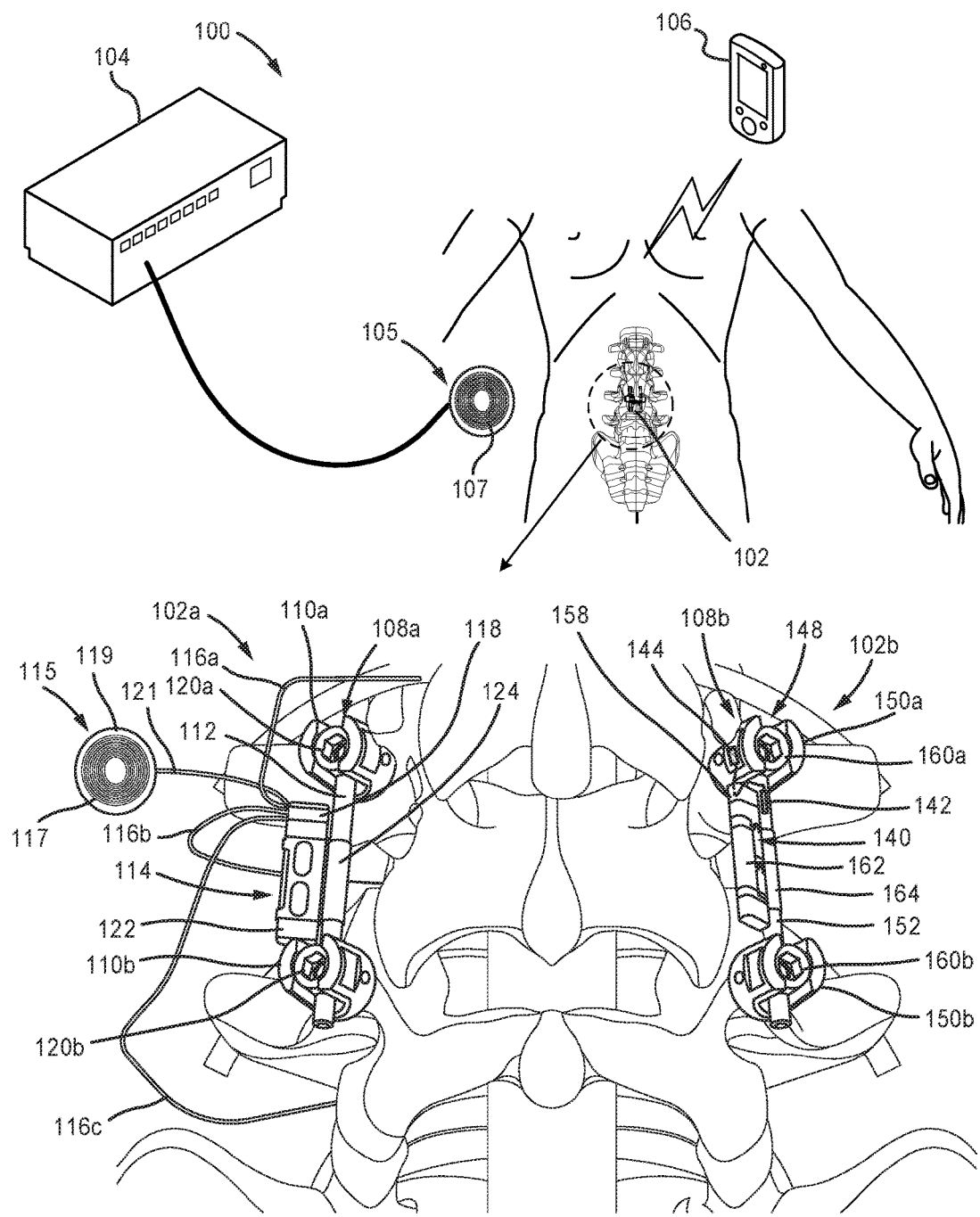
FIG. 1A is a perspective illustration of a system for delivering one or more modalities of radio frequency (RF) therapy to neural tissue in the area of an orthopedic implant device, and/or for monitoring health information related to one or more of the mechanical integrity of an orthopedic implant device and patient health.

Various systems for alleviating pain, including for example back pain or limb pain due to disease or defects of the vertebra, intervertebral disc or neural structures, are disclosed. The basic system includes: (1) an external instrument which broadcasts a radiofrequency (RF) energy field, (2) an implanted device that interacts with the energy field to convert the energy directly to heat or to electric current, and (3) probes or leads which distribute the converted energy to the anatomical target of interest. Targets of interest include neural structure, such as the dorsal root ganglion, in the area of the orthopedic implant devices.

In one embodiment, the system includes an implanted receiver that converts the RF energy field broadcast by the external instrument to electric current, and probes in the form of electrode-bearing leads, connected to the implanted receiver that are routed to the sites of therapy. The receiver may be implanted at sites in the spinal column local to the site of the pain. An example implant site is between and alongside of the interspinous processes.

In another embodiment, the system includes an implanted receiver that contains a circuit that converts the RF energy broadcast by the external instrument to a programmable pulsed RF current, and probes in the form of electrode-bearing leads, connected to the implanted receiver and routed to the sites of therapy. The receiver may be implanted at sites in the spinal column local to the site of the pain. An example implant site is between and alongside of the interspinous processes.

In another embodiment, the system includes and implanted receiver that contains a circuit that converts the RF energy broadcast by the external instrument to a programmable continuous or pulsed stimulation current in the 10 Hz to 1000 Hz range, and a probe in the form of electrode-bearing leads, connected to the implanted receiver and routed to the sites of therapy. The receiver may be implanted at sites in the spinal column local to the site of the pain. An example implant site is between and alongside of the interspinous processes.

In yet another embodiment, the system includes an implantable structure that contains an inductive circuit configured to convert the RF energy broadcast by the external instrument into heat, and a probe that delivers the heat to the sites of therapy. In this case the implantable structure may itself be a probe. For example, the implantable structure may include a heat dissipation mechanism coupled to the inductive circuit for distributing the heat to the sites of therapy. Alternatively, the system may include a probe in the form of a heat dissipating lead that is routed to the sites of therapy.

In either case, the combination implantable structure and probe, or the probes themselves, are implanted in spinal location in or adjacent to the nerves responsible for pain generation. Examples are the superior articular process of the vertebra, the annulus of the intervertebral disc, or other such location. The probe implant procedure may be an interventional method utilizing a trocar structure for inserting the probe through the tissue and releasing it at the desired location. This embodiment is based on the systems disclosed in U.S. Pat. Nos. 8,986,296 and 9,295,517, each entitled "System and Method for Generating Heat at Target Area of Patient's Body," and incorporated herein by reference.

In another aspect, the system allows for communication with smart devices, such as a smart cell phone or smart tablet, and enables the transfer, download, and capture of data information from the implanted device. This transferred and captured data may include data related to the delivery of energy and RF current, such as the time, frequency, amount and level of energy and RF current delivered. The system may also include an accelerometer or gyroscope that allows data related to movement to be transferred and captured with a smart device. The data transferred and captured from the implanted device may also be aggregated with data from peripheral devices and software applications that are independent of the implanted device. Examples of independent peripheral devices could include the GPS location that is built within a smart device and activity wearable smart device, such as a Fitbit or smart athletic shoes. Examples of independent software applications could include health apps that capture drug adherence and drug use, or health apps that capture patient surveys and health questionnaires. The data transferred and captured onto a smart device may then be aggregated and displayed on the smart device and further transferred to health information technology systems, such as electronic health records.

The features and structures of the foregoing systems and implantable structures may be combined to form embodiments configured to generate and deliver several of the various forms of therapy, e.g., stimulation current, pulsed RF current, heat, etc. Furthermore, the implantable device may be incorporated into one or more spinal fixation devices to locate the probes in the area of the target neural structure.

Accordingly, a system, may be configured to deliver one or more modalities of radio frequency (RF) therapy to neural tissue in the area of an orthopedic implant device to alleviate pain. For example, the system may deliver RF therapy in the form of RF stimulation, RF heat, or RF ablation to the dorsal root ganglion in the region of a spinal fixation device. The system may also be configured to collect and analyze health information related to implant integrity and patient health. For example, the system may analyze information indicative of the integrity or strength of an attachment between the orthopedic implant device and the patient's body, and the integrity or strength of an interconnection between component parts of the implant device to determine if corrective action is warranted, e.g., surgical procedure to strengthen attachment of implant device. The system may also collect and analyze information indicative of the range of motion and the activity level of the patient as may be affected by the implant device to determine if a change in RF therapy is warranted.

System Overview

Figure 1B:
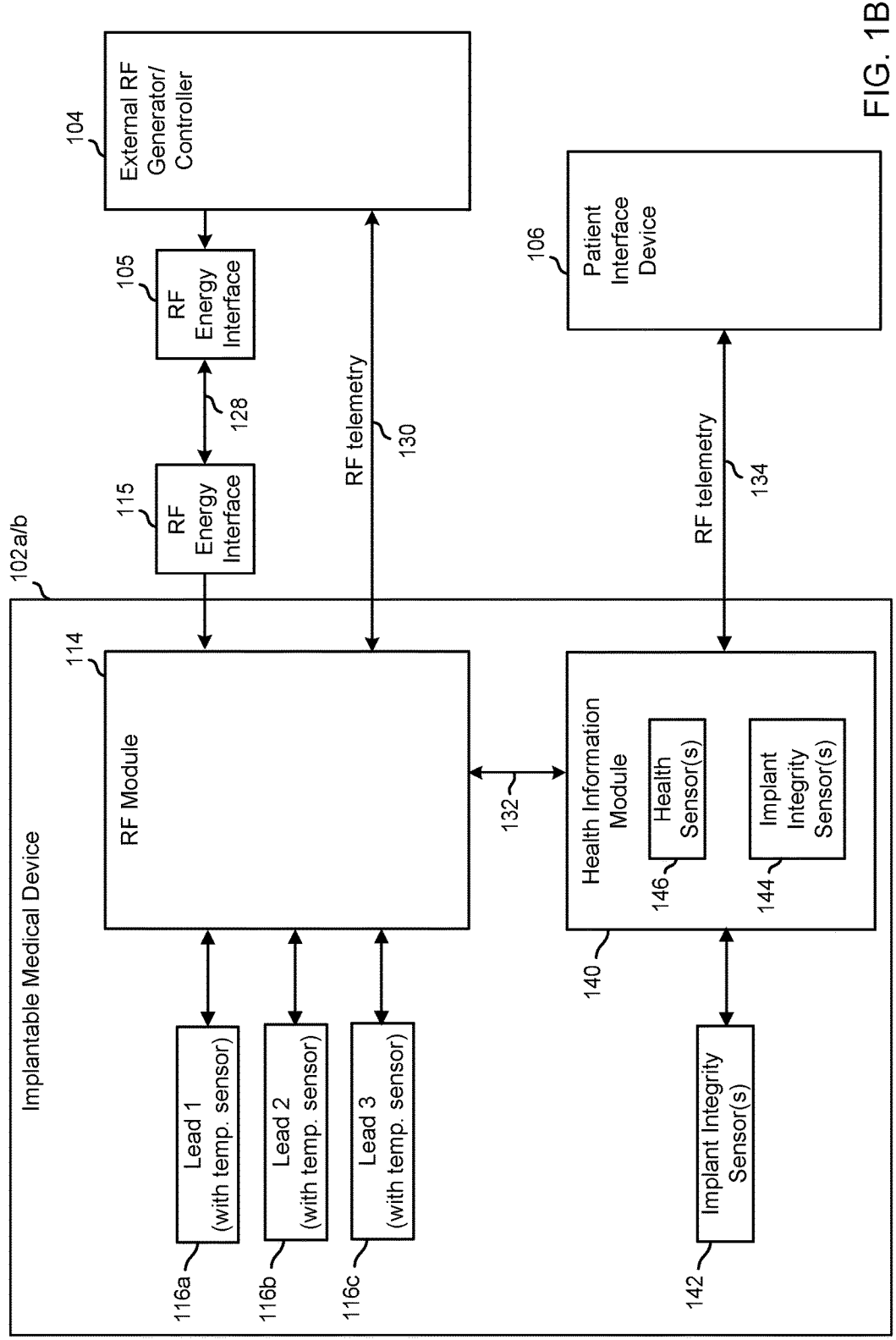
FIG. 1B is a block diagram of the system of FIG. 1A, including an implantable medical device comprising an RF module associated with one or more leads, a health information module associated with one or more sensors, and one or more external devices including an RF generator/controller and a patient interface device.

With reference to FIGS. 1A and 1B, the system 100 includes an implantable medical device 102a having an RF module 114 coupled with an implantable RF energy interface 115 that receives or admits RF energy through an inductive coil 117, and one or more electrode-bearing leads 116a, 116b, 116c for delivering RF therapy to the patient. The system 100 may also include an implantable medical device 102b having a health information module 140 associated with one or more implant-integrity sensors 142, 144 and one or more patient health sensors 146 for collecting and analyzing data, and indicating the condition of an orthopedic implant device and patient status. The implant-integrity sensors 142, 144 and patient health sensors 146 are typically included in the health information module. Some implant-integrity sensors, however, may be directly associated with the orthopedic implant device and coupled to the health information module 140 by a cable. For clarity of illustration the RF module 114 and health information module 140 are shown in FIG. 1A as separate implantable medical devices 102a, 102b. These modules, however, may be embodied in a single implantable medical device.

An external RF generator/controller 104 generates and transmits or emits RF energy through an external RF energy interface 105 that includes an inductive coil 107. The external RF energy interface 105 and the implantable RF energy interface 115, when appropriately positioned relative to each other, form a parallel-tuned resonator circuit comprising the inductive coil 107 of the external RF energy interface 105 and the inductive coil 117 of the implantable RF energy interface 115. The parallel-tuned resonator circuit provides an inductive coupling interface 128 between the external RF generator/controller 104 and the implanted RF module. The RF module 114 receives the RF energy transmitted by the RF generator/controller 104 over the inductive coupling interface 128, stores the energy, and eventually uses the energy to generate and deliver a form of RF therapy to the patient through the leads 116a, 116b, 116c.

The inductive coupling interface 128 may also facilitate data communication between the external RF generator/controller 104 and the RF module 114 for the downloading of programming information from the RF generator/controller to the RF module, and the uploading of operational information, e.g., RF therapy delivery records, from the RF module to the RF generator/controller. Alternatively, programming and data collection between the RF module 114 and the external RF generator/controller 104 may be implemented through a wireless RF telemetry interface 130. In either of the inductive coupling or the RF telemetry implementations, health information collected by the health information module 140 may also be uploaded to the external RF generator/controller 104 through a communications bus 132 that interconnects the RF module 114 and the health information module.

An external patient interface device 106 may upload health information collected by the health information module 140 through a wireless RF telemetry interface 134. Operational information, e.g., RF therapy delivery records, may also be uploaded to the external patient interface device 106 from the RF module 114 through the communications bus 132 that interconnects the RF module and the health information module 140. The external patient interface device 106 may also provide for limited operation control of the RF module 114. To this end, command signals may be sent from the patient interface device to the RF module 114 over the RF telemetry interface 134 and through the communication bus 132 to initiate the delivery of an RF therapy by the RF module, or to program the RF module to delivery an RF therapy in accordance with a therapy regimen.

RF Module and RF Therapies

Figure 1C:
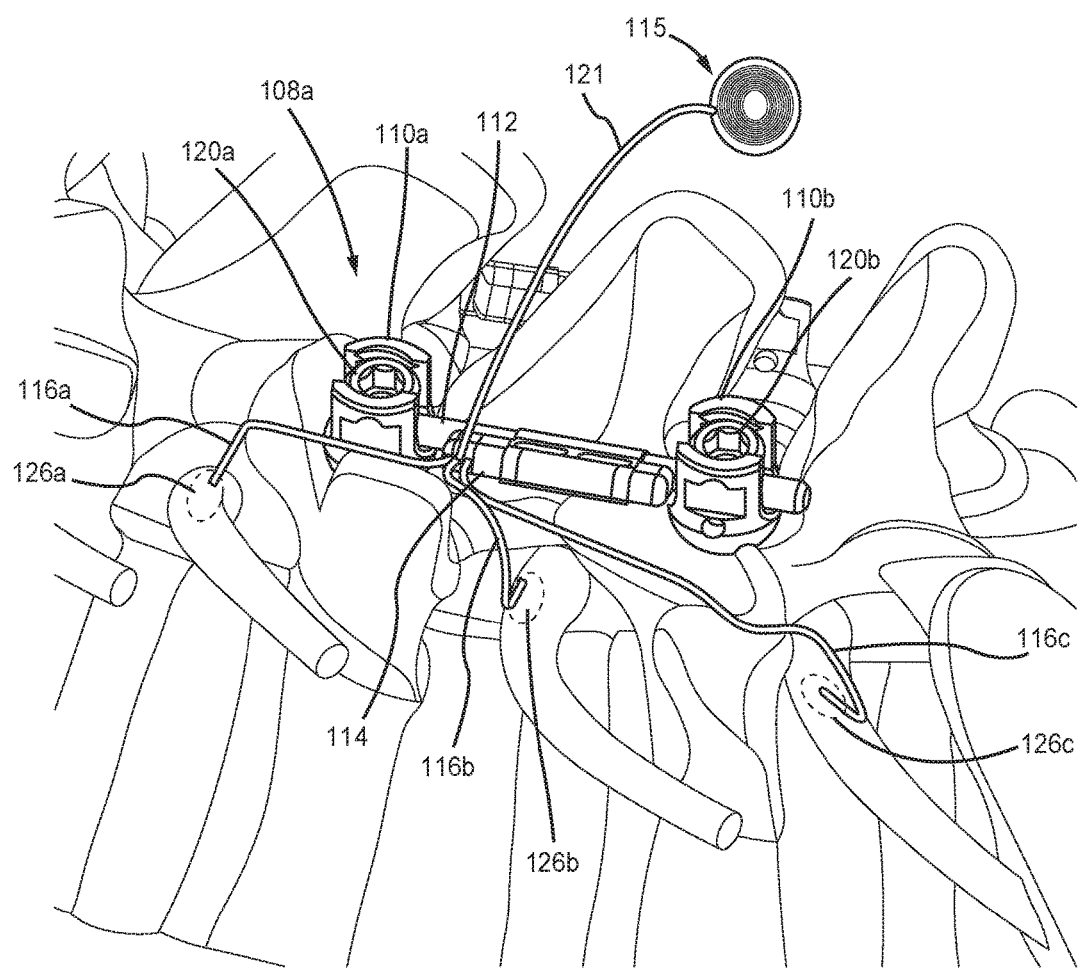
FIGS. 1C and 1D are illustrations of the implantable medical device of FIG. 1A comprising a RF module coupled to an orthopedic implant device in the form of a spinal fixation device.
Figure 1D:
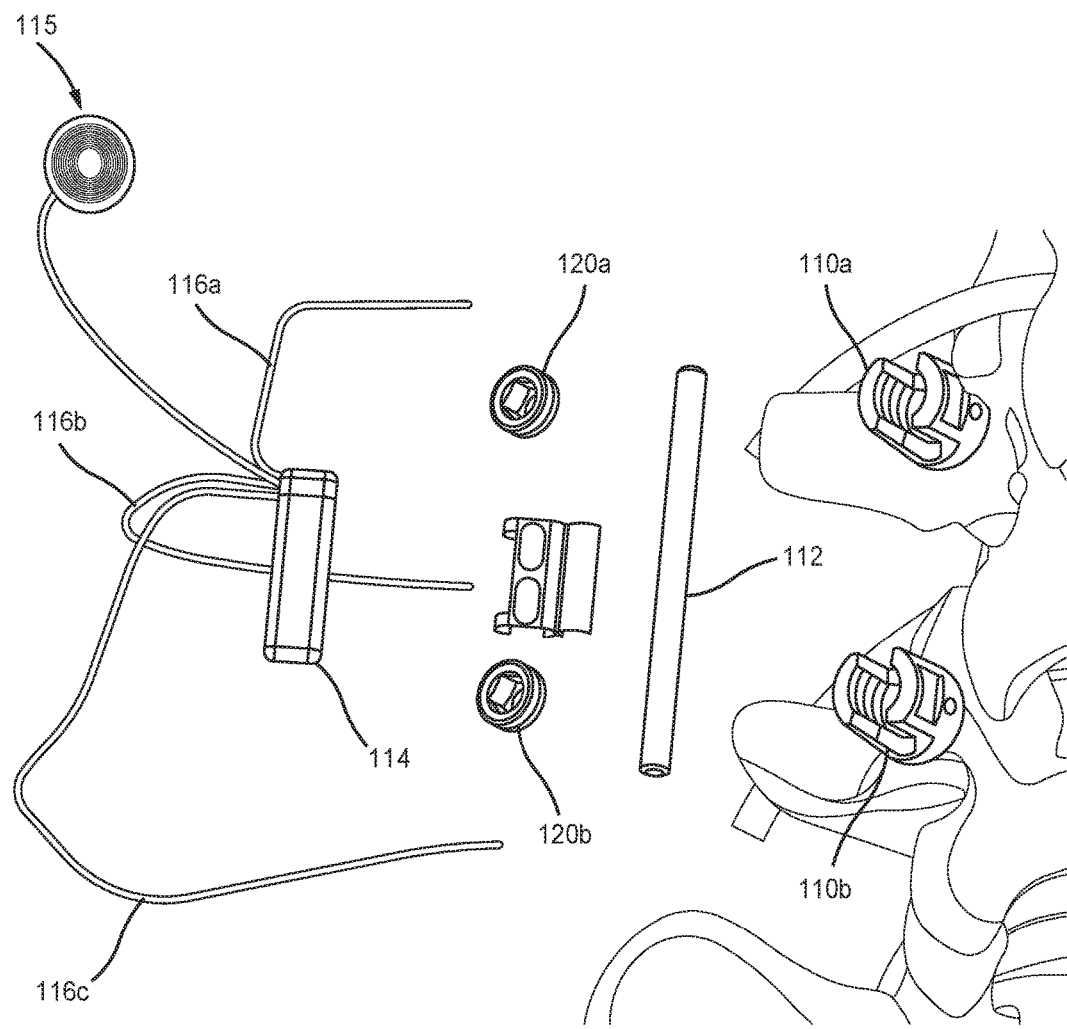

Continuing with FIGS. 1A and 1B, and with additional reference to FIGS. 1C and 1D, as just mentioned, the system 100 may include an implantable medical device 102a having an RF module 114, and an external RF generator/controller 104. In the example embodiment shown in FIGS. 1A and 1C, an implantable medical device 102 including an RF module 114, is associated with an orthopedic implant 108a in the form of a spinal fixation device implanted in the lumbar region of the spine. The spinal fixation device 108a is a rod-and-screw device that includes a pair of pedicle screws 110a, 110b and a rod 112 secured to the screws by a pair of hex nuts 120a, 120b.

The implantable medical device 102 includes the RF module 114, three electrode-bearing leads 116a, 116b, 116c, and an implantable RF energy interface 115. The RF module 114 includes a housing 122 fabricated from a biocompatible material, such as titanium, that encloses components of the RF module. The RF module 114 is secured to the rod 112 by an optional attachment mechanism 124 to prevent device migration after implant. Alternatively, the RF module 114 may be secured in place by suturing the device to the patient's anatomy. The RF module 114 may also be secured in place by anatomy itself, through appropriate positioning of the RF module in surrounding anatomy.

The leads 116a, 116b, 116c are configured to be implanted to locate one or more electrodes at their distal ends in, on, or adjacent to a target area of nerves, and to electrically couple to the RF module 114 through a connector at their proximal ends. In the example shown in FIG. 1C, the leads 116a, 116b, 116c are implanted to locate one or more electrodes in, on, or adjacent to a target area 126a, 126b, 126c corresponding to the dorsal root ganglion.

The implantable RF energy interface 115 is configured to be implanted at a subcutaneous location in the patient that is remote from the RF module 114 and the metal structures of the spinal fixation device 108a. This avoids adverse interaction between the electromagnetic field produced during the transmission and reception of RF energy over the inductive coupling interface 128, and those metal structures, which would otherwise reduce the efficiency of charging. The implantable RF energy interface 115 includes an inductive coil 117 coated or encased in polymer 119 to form a patch, and a cable 121 that connects to the RF module 114. The inductive coil 117 is formed by coiling a magnetic wire a number of turns, e.g., between 40-60 turns. In one configuration, as shown in FIG. 1A, the magnetic wire is coiled to define a circular, spiral geometry having a diameter in the range of 1-2 inches. Other coil geometries, such as rectangular, may be formed. The patch formed by the encased inductive coil 117 is flexible to allow for conformance with anatomy of a patient's back. The magnetic wire is formed by two wires tightly twisted together. The two wires emerge from the inductive coil 117 where they diverge to extend through the cable 121, and respectively connect to a separate terminal at a connector end of the cable 121.

Figure 2:
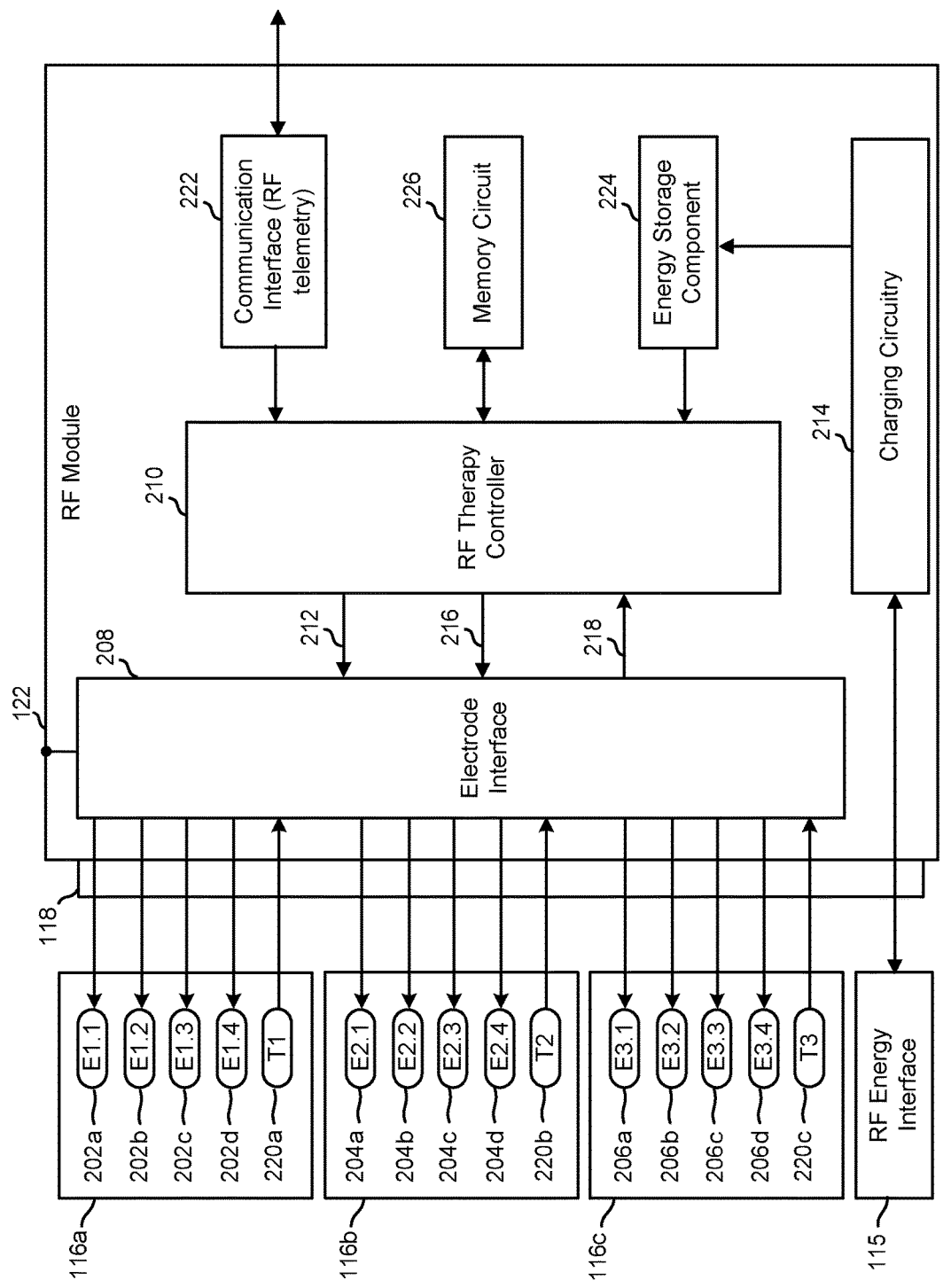
FIG. 2 is a block diagram of the RF module and leads of FIG. 1B.

FIG. 2 is a block diagram of the RF module 114, implantable RF energy interface 115, and leads 116a, 116b, 116c of FIG. 1B. The RF module 114 includes a connector 118 or header adapted to receive a connector end of each leads 116a, 116b, 116c and a connector end of the implantable RF energy interface 115. The header 118 physically secures the leads 116a, 116b, 116c to the RF module 114 and physically and electrically couples each lead and its associated, spaced-apart electrodes 202a-d, 204a-d, 206a-d to an electrode interface 208 within the RF module 114. Although twelve electrodes 202a-d, 204a-d, 206a-d are shown in FIG. 2, more electrodes may be available depending on the number of implanted leads and the number of electrodes per lead. The housing 120 is also physically coupled to the electrode interface 208 and may serve as a ground or return electrode.

The electrode interface 208 includes switch circuitry for selecting one or more lead electrodes 202a-d, 204a-d, 206a-d and housing 120 as needed for delivery of a RF therapy. The electrode interface 208 may also include circuitry that provides other features, or capabilities, including but not limited to isolation, and charge-balancing functions, that are required for a proper interface with neurological tissue.

The header 118 also physically secures the implantable RF energy interface 115 to the RF module 114 and physically and electrically couples the inductive coil 117 to charging circuitry 214 within the RF module 114. The charging circuitry 214 receives RF energy from the external RF generator/controller 104 over the inductive coupling interface 128, and provides the energy to an energy storage component 224 of the RF module. The energy storage component 224 may be a supercapacitor or one or more rechargeable batteries. The charging circuitry 214 may include a rectification circuit that causes current or voltage alternations to become monopolar with respect to a reference voltage node that connects with the parallel-tuned resonator circuit formed in part by the inductive coil 117. The charging circuitry may also include an overcharging controller, that is either automatically or externally controlled to prevent disruption or damage to the energy storage component.

An RF therapy controller 210 is coupled to the electrode interface 208 and controls the selection of electrodes by the electrode interface through control signals 212. Electrode selection by the RF therapy controller 210 may result in delivery of a modality of RF therapy through a pair of electrodes on the same lead, e.g., a bipolar electrode configuration, through one electrode on a first lead and another electrode on a second lead, e.g., a combi-polar electrode configuration, or through an electrode on a lead and the housing, e.g., a unipolar electrode configuration.

The RF module 114 also provides the form of RF signal needed to deliver a modality of RF therapy through the selected electrodes. The RF therapy controller 210 is coupled to the energy storage component 224 and configured to draw energy from the energy storage component and generate a form of RF signal commensurate with the modality of RF therapy being delivered. The RF signal 216, also referred to herein as the RF therapeutic output, is output to one or more electrodes 202a-d, 204a-d, 206a-d through the electrode interface 208. (Further description of the RF therapy controller 210 and the different modalities of RF therapy are provided below with reference to FIGS. 3-6B. Further description of the functionality of the implantable RF energy interface 115 and the charging circuitry 214 as it relates to the reception of RF energy from the external RF generator/controller is provided later below with reference to FIGS. 7A, 7B and 8.)

Continuing with FIG. 2, each of the leads 116a, 116b, 116c may also include a temperature sensor 220a, 220b, 220c configured to a provide signal indicative of the temperature at the implant location of the lead. The temperature sensors 220a, 220b, 220c are physically coupled to the electrode interface 208 through the connector 118. In one configuration, the temperature sensors 220a, 220b, 220c are located on the lead, at the distal end near the electrodes and provide a temperature feedback signal 218 to the RF therapy controller 210 to ensure that the temperature at the target area meets a specified criterion. For example, during delivery of pulsed RF stimulation therapy, the temperature at the target area should be below 42° C.; during delivery of RF heat therapy, the temperature at the target area should be within the range of 42-45° C.; and during pulsed RF ablation therapy, the temperature at the target area should be within the range of 42-45° C. If the temperature is outside of the specified range, the RF therapy controller 210 may respond by either increasing the energy of the RF therapy to increase the temperature as needed, decreasing the energy to decrease the temperature as needed, or stopping therapy delivery. Temperature feedback signals 218 may also be provided to the external RF generator/controller 104 through an RF telemetry interface 130, in which case, the RF generator/controller may output a command to the RF module 114, which causes the RF therapy controller 210 to either increase or decrease the energy of the RF therapy.

In addition to supplying energy for the generation of RF therapy signals, the energy storage component 224 supplies the voltages and currents necessary for operation of electronic components of the RF module 114, including for example, components of the electrode interface 208, the RF therapy controller 210, and the charging circuitry 214. The RF module 114 also includes a memory circuit 226. The memory circuit 226 may store information corresponding to a history of delivered RF therapies by modality type, energy storage component recharge sessions, and temperature measurements.

The RF module 114 may include a communications interface 222 that enables RF telemetry communication between the RF module and the external RF generator/controller 104 through a wireless communication link. The external RF generator/controller 104 allows a physician to program the RF therapy controller 210 with a therapy regimen. For example, the RF therapy controller 210 may be programmed to deliver periodic doses of a selected modality of RF therapy during a treatment session. The communications interface 222 also allows for the downloading of information from the memory circuit 226. Information may also be downloaded from the memory circuit 226 through the RF energy interface 115 when the interface is not receiving RF energy from the external RF generator/controller 104.

Figure 3A:
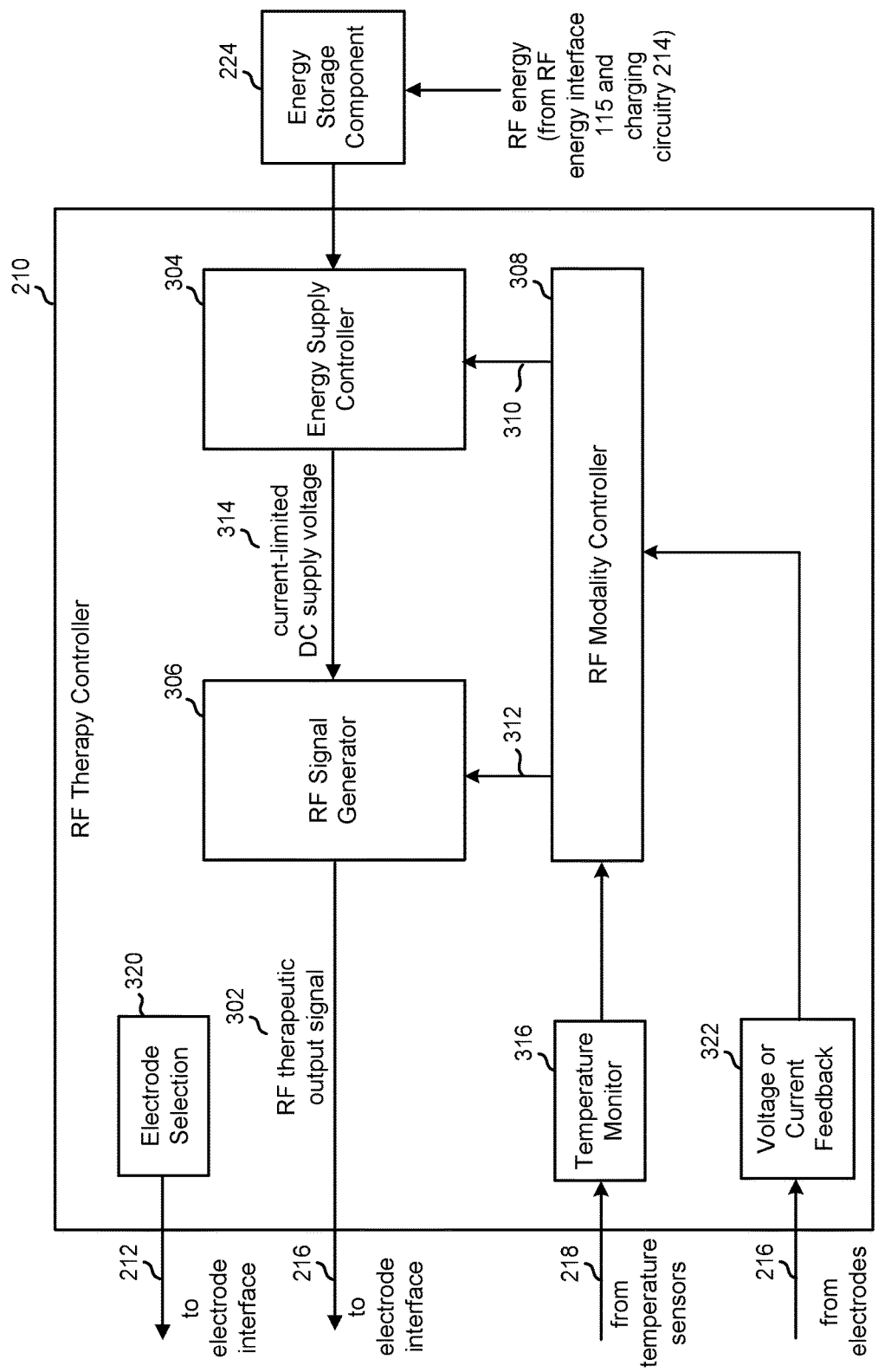
FIG. 3A is a block diagram of an RF therapy controller included in the RF module of FIG. 2.
Figure 3B:
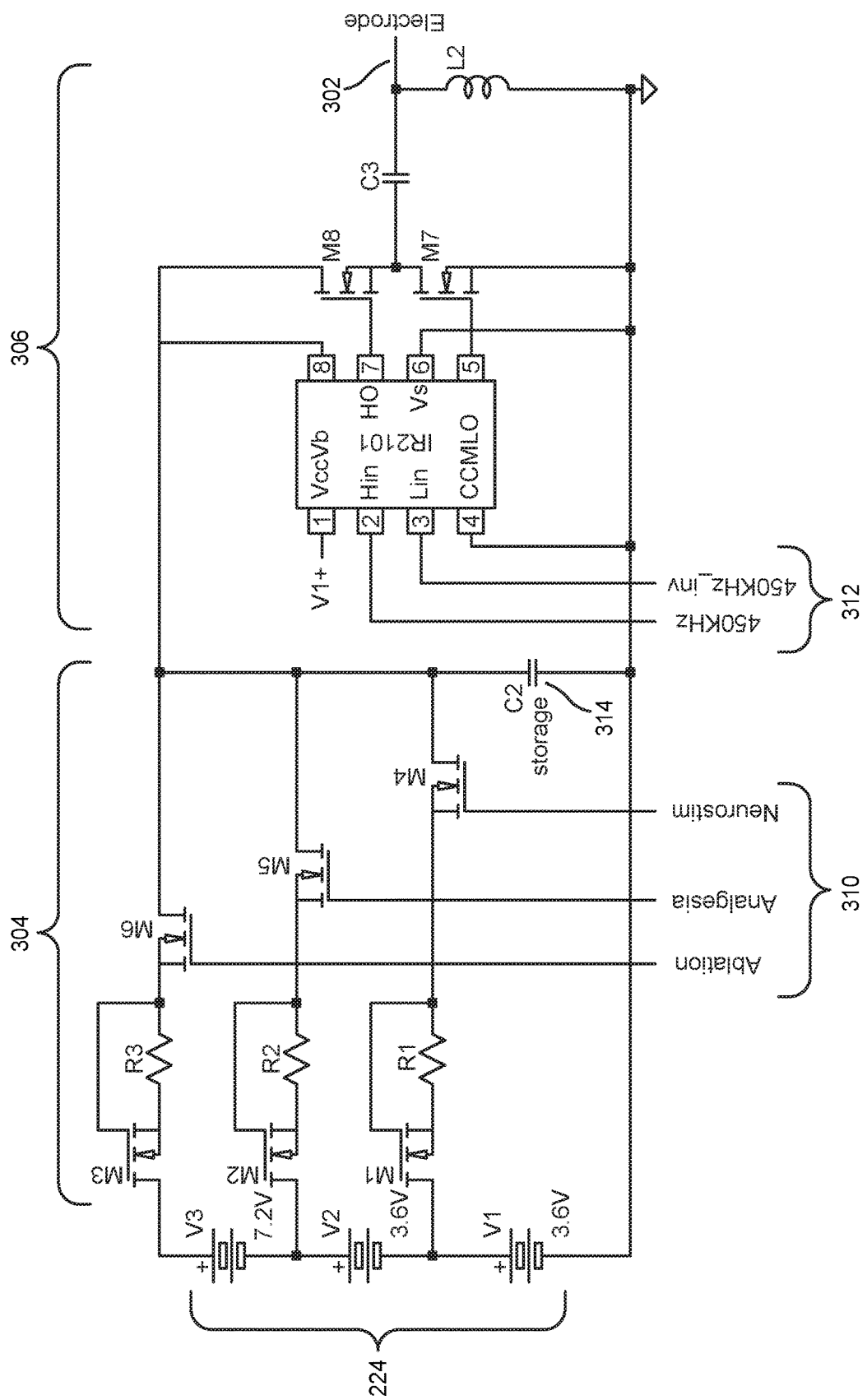
FIG. 3B is a schematic diagram of some of the components of the RF therapy controller of FIG. 3A.

With reference to FIGS. 3A and 3B, the RF therapy controller 210 includes components configured to generate a RF therapeutic output signal 302 corresponding to a selected modality of operation. The core components of the RF therapy controller 210 include an energy supply controller 304, a RF signal generator 306 and a RF modality controller 308, which provides control signals 310, 312 to the energy supply controller and the RF signal generator. Each of these control signals 310, 312 sets one or more characteristics of what will ultimately be the RF therapeutic output signal 302 of the RF therapy controller. These characteristics or parameters may include, for example, the pulse width, on/off duty cycle, therapeutic output duration, and strength, e.g., voltage output, current output, or power level, as characterized by a pulse amplitude of the RF therapeutic output signal 302.

At the input side of the RF therapy controller 210, the energy supply controller 304 is coupled to the energy storage component 224 of the RF module 114. Based on one or more control signals 310 from the RF modality controller 308, the energy supply controller 304 draws direct current or applies a voltage from the energy storage component 224 in a manner that defines one or more characteristics of the RF therapeutic output. For example, with reference to FIG. 3B, the energy supply controller 304 may include switch sets (M1/M4, M2/M5 and M3/M6) that operate in accordance with respective control signals 310 to draw direct current or apply a DC voltage from the energy storage component 224 (V1, V2 and V3) to a storage capacitor C2. For example, M1 and R1 limit current for neurostimulation to 20 mA when selected by switch M4 and control signal "Neurostim", and a DC voltage of 3.6V is applied to the storage capacitor C2. M2 and R2 limit current for analgesia to 50 mA when selected by switch M5 and control signal "Analgesia", and a DC voltage of 7.2V is applied to the storage capacitor C2. M3 and R3 limit current for ablation to 1 A when selected by switch M6 and a control signal "Ablation", and a DC voltage of 14.4V is applied to the storage capacitor C2. The control signals 310 thus determine parameters of the RF signal, including current or voltage amplitude that defines the energy per pulse or pulse strength of the RF therapeutic output signal 302. Furthermore, the on/off switching operation of the control signals 310 cause the switches M4, M5, M6 to operate in an on/off manner that ultimately defines one or more characteristics, e.g., the pulse width, duty cycle and duration, of the RF therapeutic output signal 302.

The energy stored in the storage capacitor C2 represents a current-limited DC supply voltage 314 that is applied to the RF signal generator 306. Based on control signals 312 from the RF modality controller 308, the RF signal generator 306 generates pulses of RF energy using the current-limited DC supply voltage 314 in a manner that defines one or more characteristics of the RF therapeutic output signal 302. For example, with reference to FIG. 3B, in one configuration the RF signal generator 306 may include a generic "half-bridge" switching control integrated circuit (IR2101), which applies on-off digital voltages to switches M7 and M8 to resonant excitation of L2 and C3 at the required radio frequency. The signals "450 KHz" an "450 KHz_inv" correspond to the control signals 312 that control the application of on-off digital voltages to switches M7 and M8 to thereby define the frequency of the RF signal. In this example, the control signals 312 define a frequency of 450 KHz. Through manipulation of the application of on-off digital voltages to switches M7 and M8, the control signals 312 may define other frequency values within a therapy band of 300-500 KHz. In another configuration, the RF signal generator 306 may include a voltage-controlled RF amplifier with an RF oscillator that operates in accordance with the control signals 312 to generate an RF signal within the therapy band from the current-limited DC supply voltage 314.

The combination of control signals 310, 312 provided by the RF modality controller 308 thus determines the form of the RF therapeutic output signal 302. The form of the RF therapeutic output signal 302 may correspond to one of three different modalities of RF therapy.

A first modality, referred to herein as "RF stimulation," is configured to modulate neural signals, i.e., alter or interrupt transmission of action potentials by one or more nerves, at a target area through delivery of RF signals in a pulse train form. The pulse train is defined by parameters, including RF signal frequency, pulse width, pulse amplitude, and duty cycle, which are selected to deliver pulses of alternating current (AC) to the target area, at a low current level sufficient to modulate neural signals. This RF stimulation modality of RF therapy is distinct from conventional neuromodulation systems, which modulate neural signals through delivery of electrical stimulation in the form of direct current (DC) pulses, and is advantageous over DC pulse stimulation in that the application of an RF signal avoids the accumulation of positive ions and negative ions at the interface of the membrane that may result from DC pulse stimulation.

Figure 4:
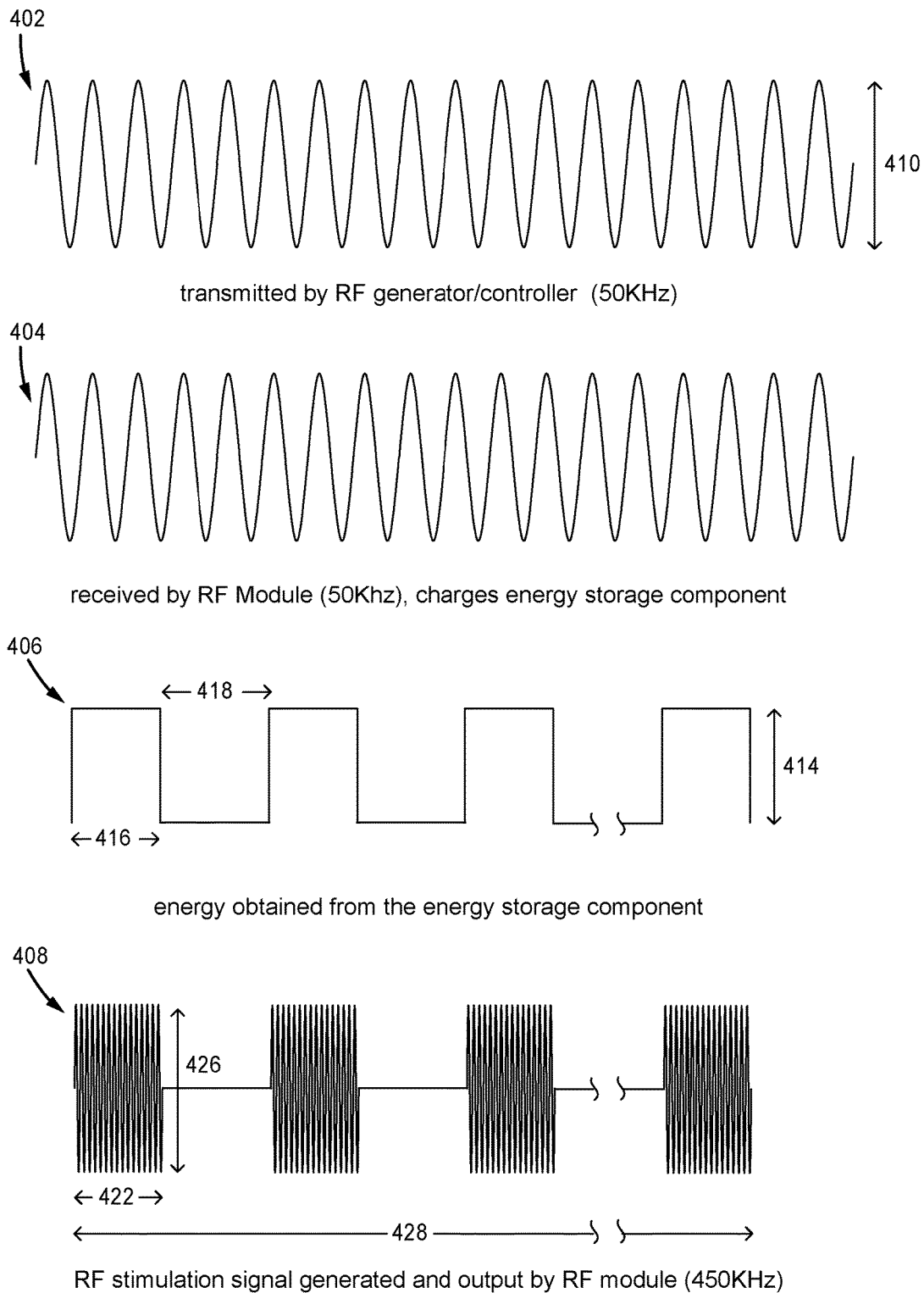
FIG. 4 includes schematic diagrams of signals involved in the generation and delivery of RF therapy in the form of neuromodulation (e.g., the RF stimulation modality) by the system and devices of FIG. 1B.

FIG. 4 includes schematic diagrams of idealized signals involved in the generation and delivery of RF therapy in the form of neuromodulation, e.g., the RF stimulation modality. With reference to FIGS. 1B, 3A and 4, the external RF generator/controller 104 generates and outputs RF energy in the form of a continuous RF signal 402. Alternatively, the RF signal 402 may be pulsed. In one embodiment, the frequency of the RF signal 402 is in a RF energy transmission band, which may be between 40-60 KHz. The RF signal 402 has a power level 410 (as represented by the amplitude) between 0.1 Watt and 10 Watts.

The RF signal 402 is transmitted to an implanted RF module 114 through transcutaneous inductive coupling. The RF signal 404 received by the RF module 114 generally maintains the same signal characteristics in terms of RF signal frequency. Although not illustrated as being attenuated, the amplitude of the received RF signal 404 may be less than the transmitted RF signal 402. For example, the amplitude of the received RF signal 404 may be attenuated by between 5% and 95%. Circuitry within the RF module 114 uses the received RF signal 404 to charge the energy storage component 224.

As described above, the RF therapy controller 210 draws current from the energy storage component 224 to charge a storage capacitor C2 to a DC voltage. The current and DC voltage are sufficient to generate at least one pulse of a RF stimulation signal. The drawn current or stored DC voltage is represented in FIG. 4 as a signal 406 alternating between on durations 416 having an amplitude 414 representing current drawn or DC voltage across the storage capacitor C2, and off durations 418 during which current is not drawn. In the example circuitry of FIG. 3B, the current is up to 20 mA and the DC voltage is 3.6V.

Using the energy present in the storage capacitor C2 during the on durations 416, the RF therapy controller 210 generates an RF therapeutic output signal 302 in the form of a RF stimulation signal 408 comprising an RF signal oscillating at a frequency in a therapy band, which may be between 400-600 KHz, and delivers the signal to the patient through one or more electrodes. The RF stimulation signal 408 is characterized by a pulse width 422 generally corresponding to the on duration 416 of the signal 406, a pulse frequency corresponding to the frequency of the on durations 416 of the current signal, a pulse amplitude 426, and a pulse-train duration 428. For example, the RF stimulation signal 408 may have a pulse frequency between 1 Hz and 10 KHz, a pulse amplitude 426 between 0.3 mA and 20 mA, a pulse width 422 of between 250 µsec and 5 µsec, and a pulse-train duration 428 between 20-30 minutes. The pulse amplitude 426 of the RF stimulation signal is selected to generate an alternating current field at or near a target area sufficient to modulate neural signals, i.e., alter or interrupt transmission of action potentials by one or more nerves, to provide pain relief, without generating too much heat to cause cell necrosis.

A second modality, referred to herein as "RF ablation," is configured to induce necrosis in cells at a target area through delivery of RF signals. This provides for a more sustained, albeit not necessarily permanent, interruption of transmission of action potentials by nerves in the target area. Like the RF stimulation modality, the RF ablation modality is provided through delivery of RF signals in a pulse train form. Alternatively, RF ablation may be provided through delivery of RF signals in a continuous form. The parameters of this pulse train form are selected to deliver enough energy to the target area to induce necrosis in cells of the nerve tissue. This necrosis-inducing level of energy may be provided, for example, through selection of parameters, e.g., pulse amplitude and pulse rate, that effect the amount of current delivered to the target area.

Figure 5:
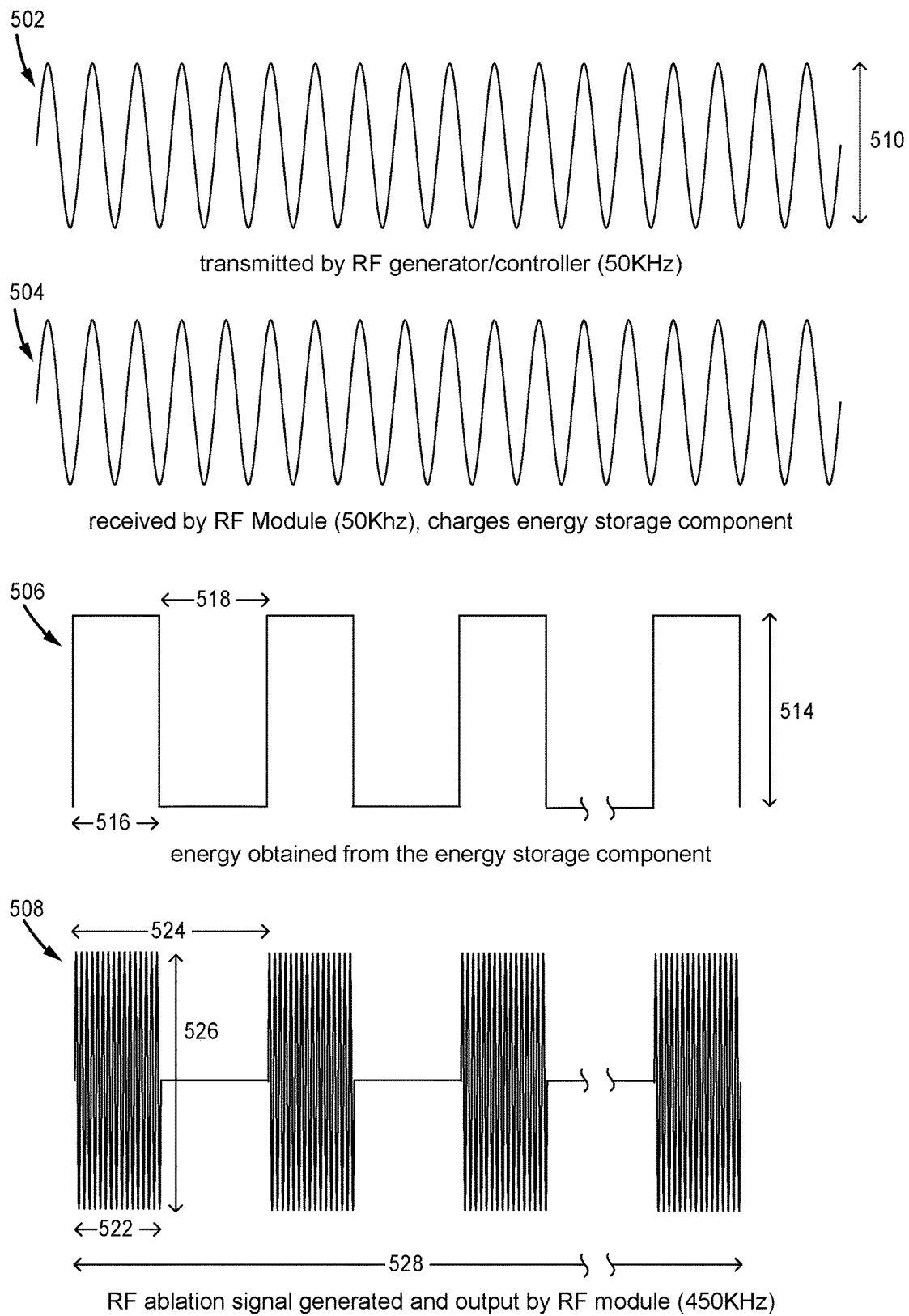
FIG. 5 includes schematic diagrams of signals involved in the generation and delivery of RF therapy in the form of ablation (e.g., the RF ablation modality) by the system and devices of FIG. 1B.

FIG. 5 includes schematic diagrams of idealized signals involved in the generation and delivery of RF therapy in the form of ablation, e.g., the RF ablation modality. With reference to FIGS. 1B, 3A and 5, the external RF generator/controller 104 generates and outputs RF energy in the form of a continuous RF signal 502. The frequency of the continuous RF signal 502 is in a RF energy transmission band, which may be between 40-60 KHz. The power level 510 (as represented by the amplitude) of the continuous RF signal 502 may be in the range of 0.1 Watt to 10 Watts.

The continuous RF signal 502 is transmitted to an implanted RF module 114 through transcutaneous inductive coupling. The RF signal 504 received by the RF module 114 generally maintains the same signal characteristics in terms of RF signal frequency. Although not illustrated as being attenuated, the amplitude of the received RF signal 504 may be less than the amplitude 510 transmitted continuous RF signal 502. For example, the amplitude of the received RF signal 504 may be attenuated by between 5% and 95%. Circuitry within the RF module 114 uses the received RF signal 504 to charge the energy storage component 224.

As described above, the RF therapy controller 210 draws current from the energy storage component 224 to charge a storage capacitor C2 to a DC voltage. The current and DC voltage are sufficient to generate at least one pulse of a RF ablation signal. The drawn current or stored DC voltage is represented in FIG. 5 as a signal 506 alternating between on durations 516 having an amplitude 514 representing current drawn or DC voltage across the storage capacitor C2, and off durations 518 during which current is not drawn. In the example circuitry of FIG. 3B, the current is up to 1 A and the DC voltage is 14.4V.

Using the energy present in the storage capacitor C2 during the on durations 516, the RF therapy controller 210 generates an RF therapeutic output signal 302 in the form of a RF ablation signal 508 comprising an RF signal oscillating at a frequency in a therapy band, which may be between 400-600 KHz, and delivers the signal to the patient through one or more electrodes. The RF ablation signal 508 is characterized by a pulse width 522 generally corresponding to the on duration 516 of the signal 506, a duty cycle 524 defined by the on duration 516 and the off duration 518 of the current signal, a pulse amplitude 526, and a pulse-train duration 528. For example, the RF ablation signal 508 may have a duty cycle 524 up to 50%, a pulse amplitude 526 between 45V and 100V, a pulse width 522 of 0.050 msec on and 0.050 msec off, a pulse frequency of up to 10 Hz, and a pulse-train duration 528 of 180 seconds. The pulse amplitude 526 of the RF ablation signal is selected to generate a voltage field at or near a target area through the delivery of alternating current that generates heat resulting in elevated temperature that cause nerve cell necrosis.

A third modality, referred to herein as "RF heat," is configured to increase the temperature at a target area of neural tissue to provide analgesic heat to alleviate pain. This modality is provided through delivery of a continuous RF signal. The parameters of this signal are selected to deliver enough energy to the target area to heat the nerve tissue. This heat-inducing level of energy may be provided, for example, through selection of an amplitude or energy level that effects the amount of current delivered to the target area.

Figure 6:
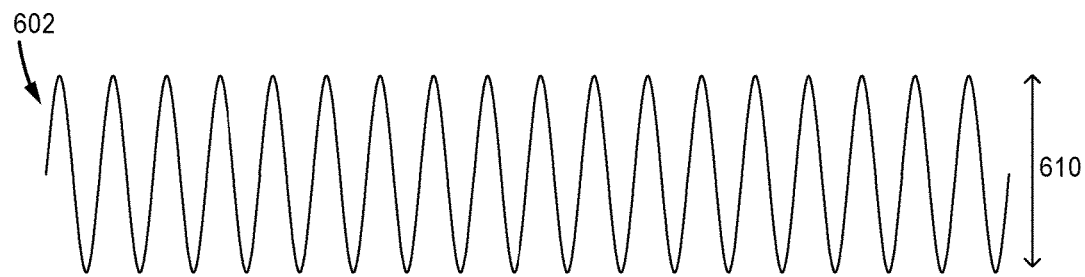
FIG. 6 includes schematic diagrams of signals involved in the generation and delivery of RF therapy in the form of heat (e.g., the RF heat modality) by the system and devices of FIG. 1B.
Figure 6:
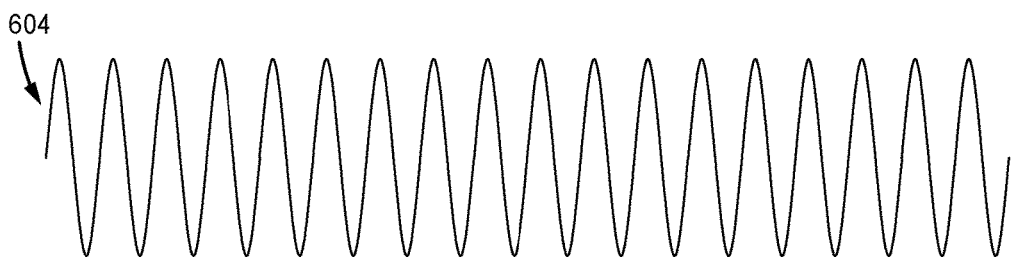
Figure 6:
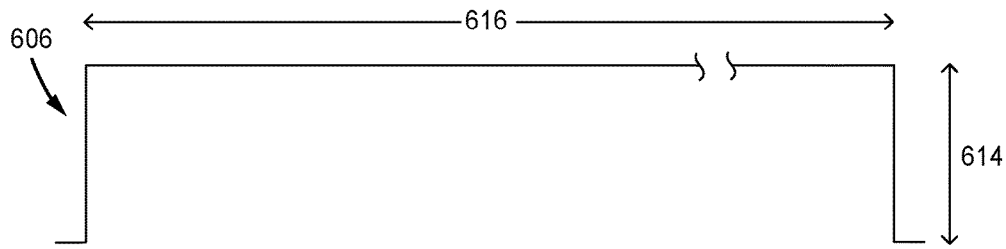
Figure 6:
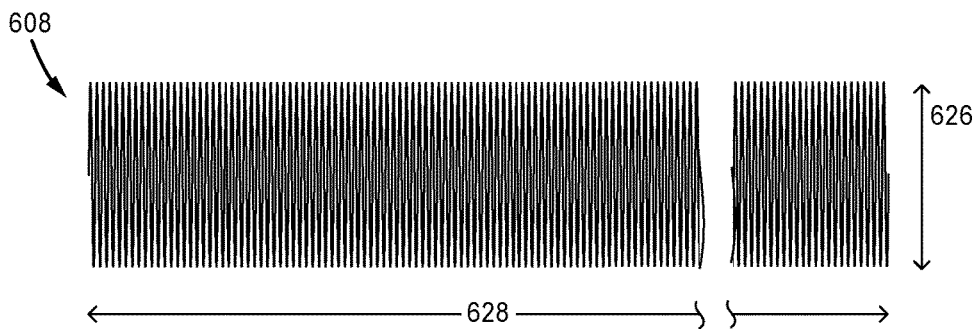

FIG. 6 includes schematic diagrams of idealized signals involved in the generation and delivery of RF therapy in the form of heat, e.g., the RF heat modality. With reference to FIGS. 1B, 3A and 6, the external RF generator/controller 104 generates and outputs RF energy in the form of a continuous RF signal 602. The frequency of the continuous RF signal 602 is in a RF energy transmission band, which may be between 40-60 KHz. The power level 610 (as represented by the amplitude) of the continuous RF signal 602 may be in the range of 0.1 Watt to 10 Watts.

The continuous RF signal 602 is transmitted to an implanted RF module 114 through transcutaneous inductive coupling. The RF signal 604 received by the RF module 114 generally maintains the same signal characteristics in terms of RF signal frequency. Although not illustrated as being attenuated, the amplitude of the received RF signal 604 may be less than the amplitude 610 of the transmitted RF signal 602. For example, the amplitude of the received RF signal 604 may be attenuated by between 6% and 96%. Circuitry within the RF module 114 uses the received RF signal 604 to charge the energy storage component 224.

As described above, the RF therapy controller 210 draws current from the energy storage component 224 to charge a storage capacitor C2 to a DC voltage. The current and DC voltage are sufficient to generate a continuous RF heat signal. The drawn current or stored DC voltage is represented in FIG. 6 as a signal 606 having a continuous on duration 616 and an amplitude 614 representing current drawn or DC voltage across the storage capacitor C2. In the example circuitry of FIG. 3B, the current is up to 50 mA and the DC voltage is 7.2V.

Using the energy present in the storage capacitor C2 during the on duration 616, the RF therapy controller 210 generates an RF therapeutic output signal 302 in the form of a continuous RF heat signal 608 comprising an RF signal oscillating at a frequency in a therapy band, which may be between 400-600 KHz, and delivers the signal to the patient through one or more electrodes. The RF heat signal 608 is characterized by an amplitude 626 and a duration 628. For example, the RF heat signal 608 may have an amplitude 626 between 1 mA and 50 mA and a duration 628 of 20-30 minutes. The pulse amplitude 626 of the RF heat signal is selected to generate a current field at or near a target area through the delivery of alternating current that generates heat, without causing nerve cell necrosis.

Returning to FIG. 3A, the RF therapy controller 210 includes a temperature module 316 that functions as a safety module that triggers an adjustment in the output of the RF therapy controller 210 based on temperature feedback provided by the temperature sensors on the leads. To this end, if a temperature feedback signal 218 received by the temperature module 316 indicates a temperature that exceeds a maximum acceptable temperature, the temperature module 316 may respond by sending an alert signal to the RF modality controller 308 that causes the RF modality controller to manipulate the control signals 310, 312 in a way that either stops the RF therapeutic output signal 302 from being provided to the electrode interface, or that adjusts one or more parameters, e.g., pulse width, duty cycle, amplitude, etc., of the RF therapeutic output signal to reduce the energy being delivered, which should in turn, reduce the temperature.

The electrode selection module 320 controls the selection of electrodes by the electrode interface 208 through control signals 212. The electrode selection module 320 may be set, through programming by the external RF generator/controller 104, to select one or more of: 1) a pair of electrodes on the same lead to form a bipolar electrode configuration for delivery of a modality of RF therapy through, 2) one electrode on a first lead and another electrode on a second lead to form a combi-polar electrode configuration for delivery of a modality of RF therapy, or 3) an electrode on a lead and the housing to form a unipolar electrode configuration for delivery of a modality of RF therapy. Depending on the RF therapy being delivered, more than two electrodes may be selected. For example, when delivering RF heat therapy or RF ablation in a bipolar electrode configuration, multiple pairs of electrodes may be selected to spread the thermal power deposition over a larger volume of nerve tissue. Similarly, when delivering RF heat therapy or RF ablation in a unipolar electrode configuration, multiple electrodes on one or more lead may be selected.

The voltage or current feedback module 322 monitors either of voltage or current at the one or more electrode through which RF therapy is being delivered depending on whether the RF module is functioning as a current controlled device or a voltage controlled device. In the case of a current controlled device, the voltage potential between a pair of electrodes delivering the therapy is monitored and varied as needed to deliver the prescribed amount of current to the target area. For example, during RF stimulation the amount of current deposited through the electrodes should be maintained within a low-level range, such as between 0.3 mA and 20 mA, sufficient to modulate neural signals without heating tissue. In the case of a voltage controlled device, the voltage potential between a pair of electrodes delivering the therapy is monitored and the amount of current being delivered is varied as needed to maintain a prescribed voltage field in the target area. For example, during RF ablation the amount of current deposited through the electrodes will be varied as need to maintain a voltage field in the target area, in the range of 45V and 60V, sufficient to heat tissue and cause nerve cell necrosis.

Figure 7A:
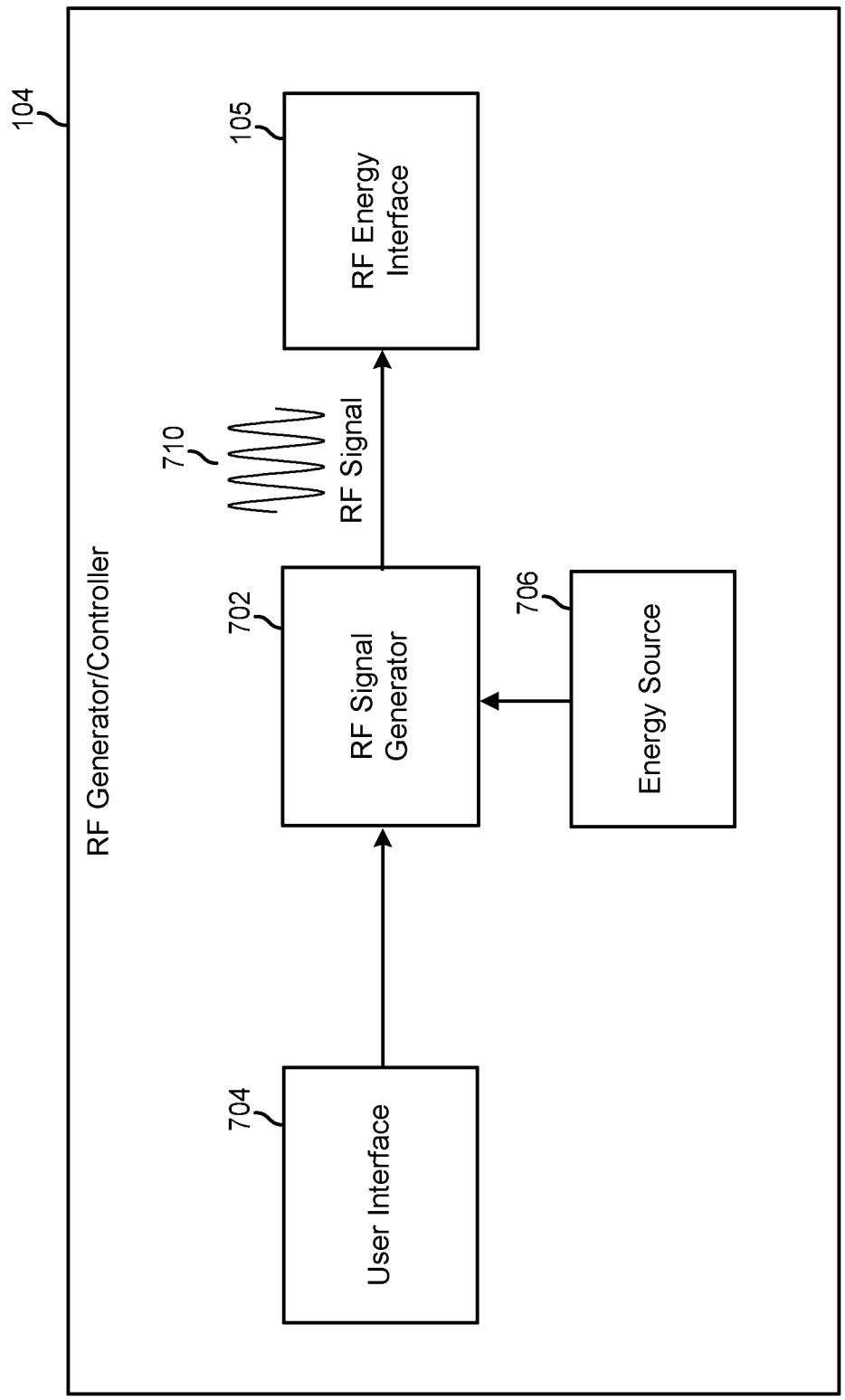
FIG. 7A is a block diagram of the external RF generator/controller of FIG. 1B.
Figure 7B:
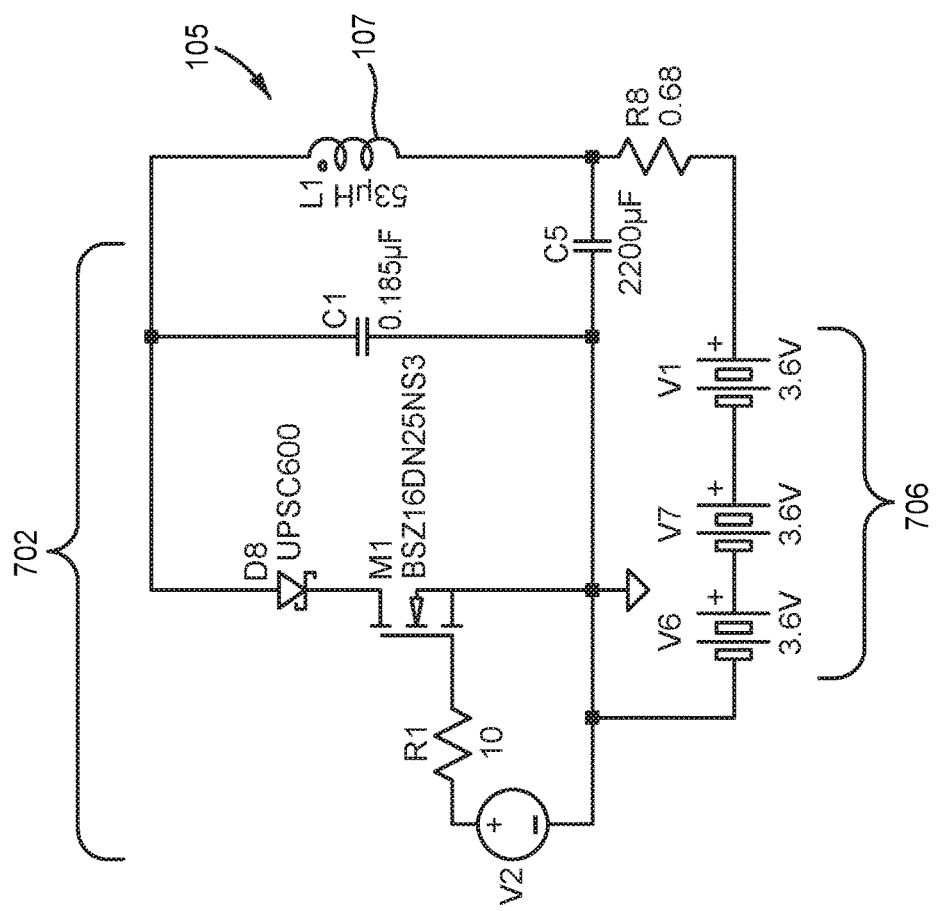
FIG. 7B is a schematic diagram of some of the components of the external RF generator/controller of FIG. 7A.

With reference to FIGS. 7A and 7B, the external RF generator/controller 104 includes a RF signal generator 702 that generates an RF signal 710 by drawing current from an energy source 706. The RF signal 710 is generated by the RF signal generator 702 in accordance with parameters specified through a user interface 704. The user interface 704 allows for a user to specify RF signal parameters, including RF signal frequency and amplitude. Additional parameters, which may be specified include pulse width, pulse frequency, duty cycle, and pulse-train duration. Alternatively, the user interface may allow a user to select a modality of RF therapy to be delivered, in which case the RF signal generator 702 will automatically determine the RF signal 710 parameters.

With reference to FIG. 7B, the RF signal generator 702 includes electronic circuitry, e.g., amplifiers, oscillator, resonators, that generate the RF signal 710. The energy source 706 includes one or more batteries, which may be recharged through an external AC power supply (not shown). A pulse generator V2 provides a pulse output that controls the on/off state of a switch M1. When the output of V2 is high, a pulse of current is drawn through the inductor L1 from the DC batteries V1, V6, V7. When the output of V2 goes low, the switch M1 switches off and the energy stored in the inductor L1 resonates with the capacitor C1 resulting in a sine wave current that goes back and forth between the inductor L1 and capacitor C1. The frequency of the sine wave is determined by the values of inductor L1 and capacitor C1, which may be chosen to provide a sine wave having a frequency in the RF energy band, e.g., 40-60 KHz. The amplitude of the sine wave current is determined by the variable pulse width and duty cycle of the pulse generator V2 output. The output of the RF signal generator 702 is provided to the RF energy interface 105. The RF energy interface 105 functions as an energy transmitter that applies the RF signal to an inductive coil 107 to emit or transmit RF energy.

Figure 8:
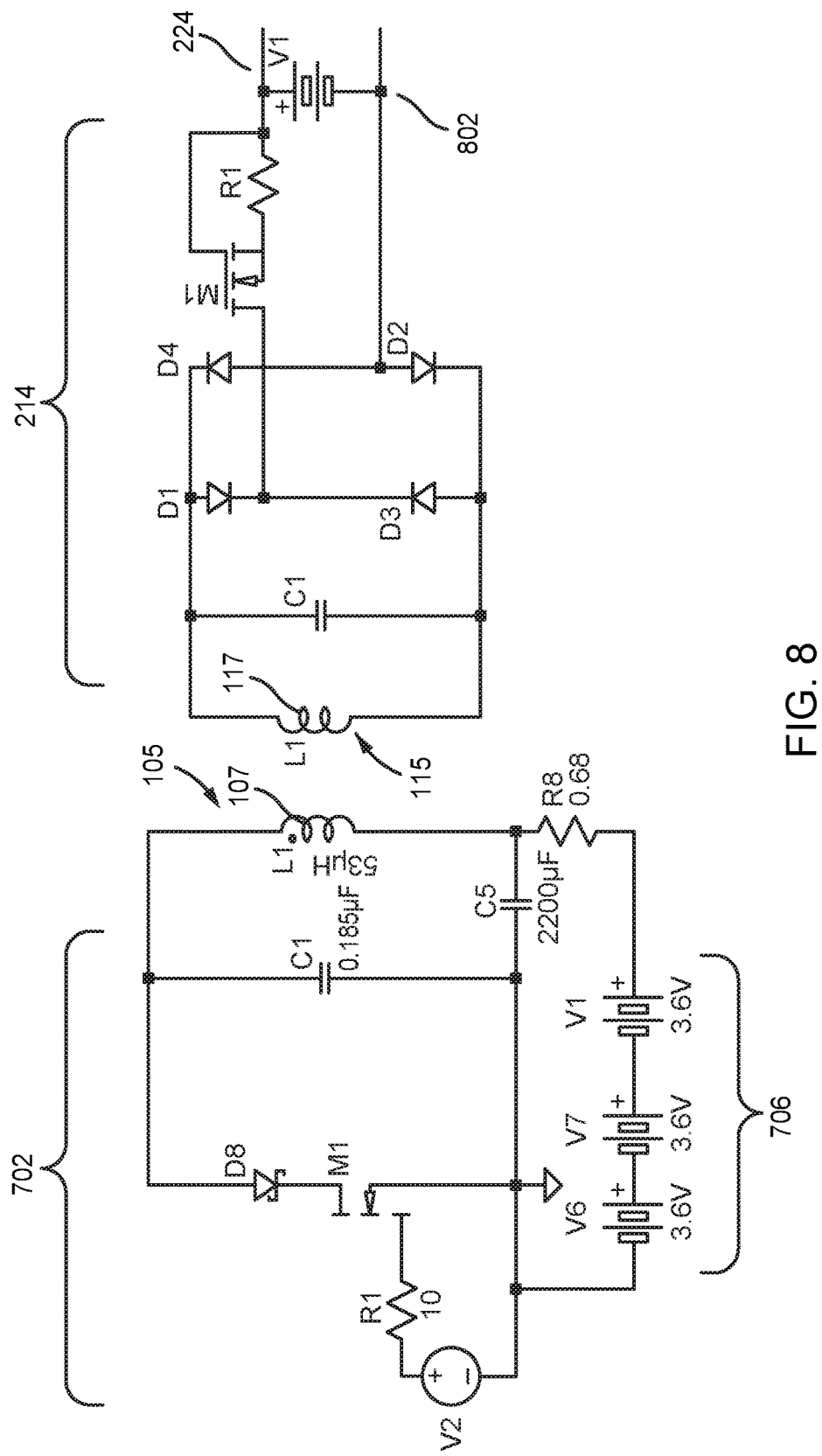
FIG. 8 is a block diagram of an RF energy link between the RF module and the external RF generator/controller of FIG. 1B that allows for wireless, transcutaneous transmission of RF energy between the external RF generator and the RF module.

FIG. 8 is a schematic diagram of an RF energy link between the RF module 114 of FIG. 2 and the external RF generator/controller 104 of FIGS. 7A and 7B that allows for wireless, transcutaneous transmission of RF energy between the external RF generator/controller and the RF module. The RF energy link is provided by the external RF energy interface 105 that may be in the form of a wand connected to the external RF generator/controller 104, and an implanted RF energy interface 115 that is connected to the RF module 114. Each of the interfaces includes an inductive coil 107, 117. During energy exchange, the inductive coil 107 of the external RF energy interface 115 is orientated to be plane-parallel to the inductive coil 117 of the implantable RF energy interface 115 and center-to-center aligned, with separation as small as possible for optimum efficiency of power transfer. The inductive coil 107 of the external RF energy interface 105 may be referred to as a primary coil, external coil, or transmit coil, while the inductive coil 117 of the implanted RF energy interface 115 may be referred to as a secondary coil, interior coil, or receive coil. The external RF energy interface 105 receives the RF signal generated by the RF signal generator 702 and includes circuitry that couples to the terminals of the external transmit coil 107. The implanted receive coil 117 of the implantable RF energy interface 115 couples to the charging circuitry 214 of the RF module 114.

As previously described, the charging circuitry 214 includes a rectification circuit (formed by diodes D1, D2, D3, D4) that causes current or voltage alternations to become monopolar with respect to a reference voltage node 802 that connects with the parallel-tuned resonator circuit formed in part by the inductive coil 117. The charging circuitry 214 may also include an overcharging controller (formed by M1 and R1), that is either automatically or externally controlled to prevent disruption or damage to the energy storage component 224.

Energizing the transmit coil 107 in the external RF energy interface 105 means drawing an alternating current through that coil. The alternating current creates a magnetic field around the external RF energy interface 105, which induces an alternating voltage across the terminals of the receive coil 117 of the implanted RF energy interface 115. When the receive coil 117 terminals connect with an electrical load included in the charging circuitry 214, power may be extracted from the receive coil 117. The power may be used to power internal electronics or to charge an implanted energy storage component 224. This process of energy transfer is called: "inductive coupling."

The external RF generator/controller 104 may be configured to operate in conjunction with an implanted RF module 114 to provide the energy needed by the RF module to deliver a modality of RF therapy. It may also be configured to provide RF therapy in the form of diathermy independent of the RF module. Thus, the external RF generator/controller 104 is configurable to operate in two modes: 1) a charging mode during which it provides energy to the RF module, and 2) a diathermy mode during which it delivers energy directly to the patient.

Regarding the charging mode, as described above with reference to FIGS. 4, 5 and 6, the external RF generator/controller 104 may transmit RF energy through inductive coupling through the application of a RF signal to an inductor. The energy is captured by the RF module 114 and may be used to deliver either one of RF stimulation, RF ablation, or RF heat to the patient through electrodes coupled to the RF module. The application of the RF signal to the inductor is typically continuous thus resulting in continuous charging of the energy storage component of the RF module, even while RF therapeutic output signals are being generated and delivered by the RF module. Alternatively, the RF signal generated by the external RF generator/controller 104 may be transmitted in pulses over the course of a therapy session.

Regarding the diathermy mode, the external RF generator/controller 104 may be configured to delivery diathermy directly to the patient—independent of the RF module. In this mode of therapy delivery, the external RF energy interface is placed on the surface of the patient to position the coil of the external RF energy interface at a location remote from the implanted receiving coil. An RF diathermy signal is generated by the RF generator/controller 104 and applied to the external coil. The RF diathermy signal may be transmitted continuously and have a frequency in the energy transmission band, e.g., 40-60 KHz, and with a voltage and current characteristics that result in a power deposition into tissue up to. 5 Watts/cm$^3$.

Figure 9:
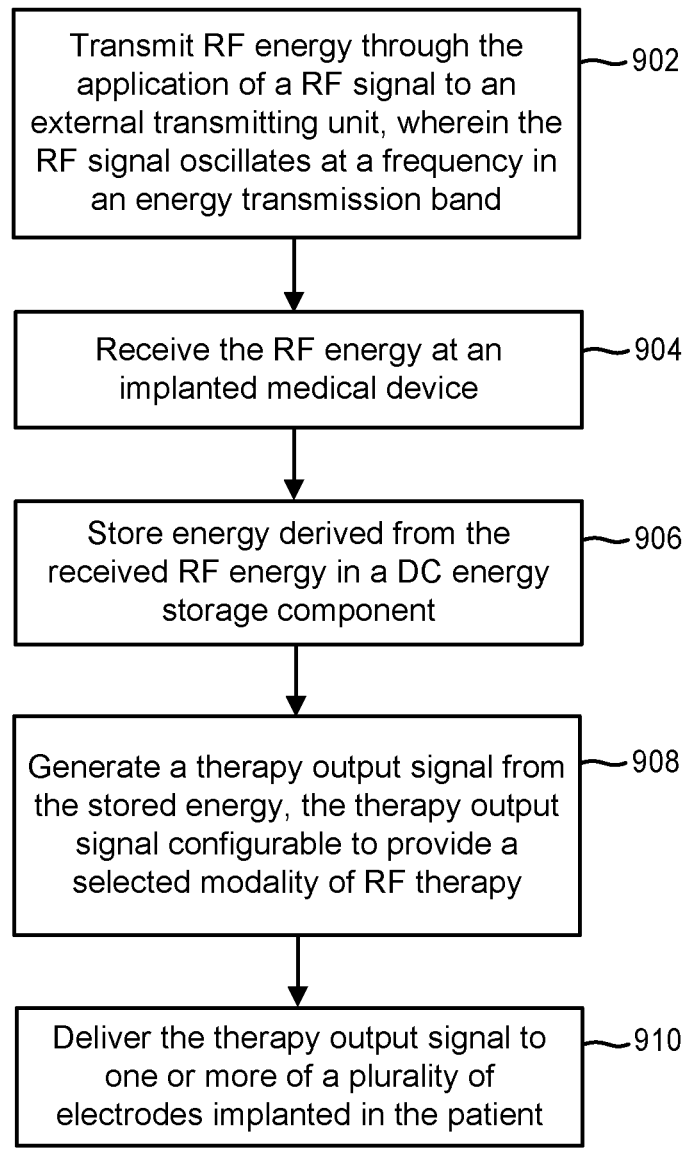
FIG. 9 is a flow chart of a method of delivering RF therapy to a patient.

FIG. 9 is a flowchart of a method of delivering RF therapy to a patient, which may be implemented using the system and devices described above. The RF therapy may be selected from among different modalities including RF stimulation, RF ablation and RF heat.

At block 902, RF energy is transmitted by an external device, such an external RF generator/controller 104 through the application of a RF signal to an external RF energy interface. The RF signal oscillates at a frequency in an energy transmission band, which may be between 40 KHz and 60 KHz. The RF signal is transmitted continuously. Alternatively, the RF signal may be transmitted in pulses.

At block 904, the transmitted RF energy is received at an implanted medical device through transcutaneous inductive coupling. At block 906, energy derived from the received RF energy is stored in an energy storage component of the implanted medical device. The energy storage component may be a supercapacitor or a DC battery.

At block 908, a therapeutic output signal is generated from the energy stored in the energy storage component. The therapeutic output signal is configurable to provide the selected modality of RF therapy. For example, if RF stimulation therapy is the selected modality, the implanted medical device generates a RF therapeutic output signal 302 in the form of a RF stimulation signal 408 such as shown in FIG. 4. If RF ablation therapy is the selected modality, the implanted medical device generates a RF therapeutic output signal 302 in the form of a RF ablation signal 508 such as shown in FIG. 5. If RF heat therapy is the selected modality, the implanted medical device generates a RF therapeutic output signal 302 in the form of a RF heat signal 608 such as shown in FIG. 6. In all cases the generated signals are characterized by an RF signal oscillating at a frequency in a therapy band, which may be between 400 KHz and 600 KHz.

At block 910, the therapy output is delivered to one or more of a plurality of electrodes implanted in the patient. To this end, the RF therapy controller 210 selects one or more electrodes through which to deliver the therapy signal. As mentioned previously, the electrode selection by the RF therapy controller 210 may result in delivery of a modality of RF therapy through a pair of electrodes on the same lead, e.g., a bipolar electrode configuration, through one electrode on a first lead and another electrode on a second lead, e.g., a combi-polar electrode configuration, or through an electrode on a lead and the housing, e.g., a unipolar electrode configuration. In any case, one of the electrodes is coupled to ground, and the RF therapeutic output signal 302 in the form of a RF signal 408, 508, 608 is applied to the other electrode to create an alternating current field or voltage field between the electrodes.

In some implementations, more than one modality of RF therapy may be delivered to a patient, either one after another, or simultaneously. In one application, therapies may be delivered in series, with the most benign therapy being applied first. For example, RF stimulation may be applied before either of RF heat or RF ablation. If RF stimulation does not provide the intended relief, then one of RF heat or RF ablation may be applied next. In the case of delivering different therapies simultaneously, for example, RF stimulation together with RF heat, the RF therapy controller may select one pair of electrodes for delivery of RF stimulation and another set of electrodes for delivery of RF heat. Additional circuitry and components may be needed to provide simultaneous delivery of therapies. For example, parallel circuitry may be included in the RF therapy controller 210 to generate two different types of RF therapeutic outputs 302. In the case of simultaneous RF stimulation and diathermy, two external RF energy interfaces 115 may be needed, one to output RF energy for diathermy and the other to output RF energy in the energy transmission band for delivery to the RF module.

Implant Integrity and Patient Health Monitoring

Figure 1E:
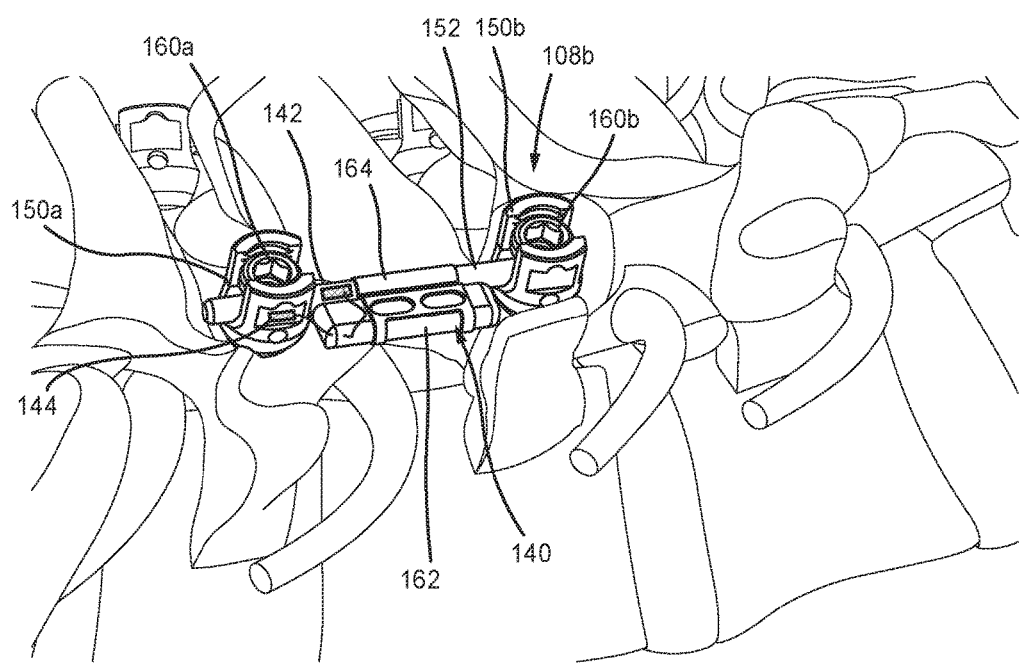
FIGS. 1E and 1F are illustrations of the implantable medical device of FIG. 1A comprising a health information module coupled to an orthopedic implant device in the form of a spinal fixation device.
Figure 1F:
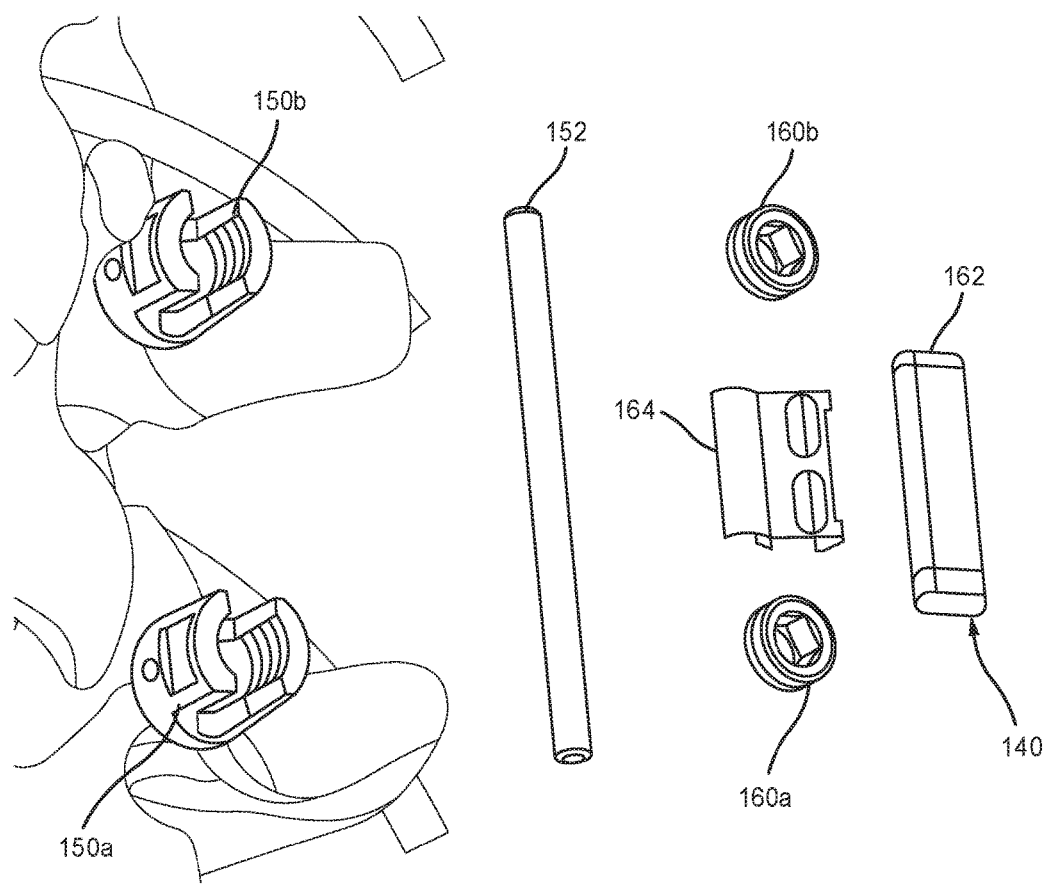

Returning to FIGS. 1A and 1B, and with additional reference to FIGS. 1E and 1F, as generally described above, the system 100 may include a health information module 140 associated with one or more implant-integrity sensors 142, 144 and one or more patient health sensors 146 for collecting and analyzing data, and indicating the condition or mechanical integrity of the orthopedic implant device and patient status. In the example embodiment shown in FIGS. 1A, 1E and 1F, an implantable medical device 102 including a health information module 140 is associated with an orthopedic implant 148 in the form of a spinal fixation device implanted in the lumbar region of the spine. The spinal fixation device 148 is in the form of a rod-and-screw device and includes a pair of pedicle screws 150a, 150b and a rod 152 secured to the screws by a pair of hex nuts 160a, 160b.

The implantable medical device 102 includes a health information module 140 having one or more implant-integrity sensors 142, 144 and one or more patient health sensors 146. The health information module 140 includes a housing 162 fabricated from a biocompatible material, such as titanium, that encloses components of the health information module. The health information module 140 is secured to the rod 152 by an optional attachment mechanism 164 to prevent device migration after implant. Alternatively, the health information module 140 may be secured in place by suturing the device to the patient's anatomy. The health information module 140 may also be secured in place by anatomy itself, through appropriate positioning of the RF module in surrounding anatomy. In the example shown in FIG. 1A, implant-integrity sensor 142, 144 are associated with components of the implant device and are coupled to the housing of the health information module 140 by cables. Other implant-integrity sensors may be included within or on the housing 162. Patient health sensors may be included within or on the housing 162.

Figure 10:
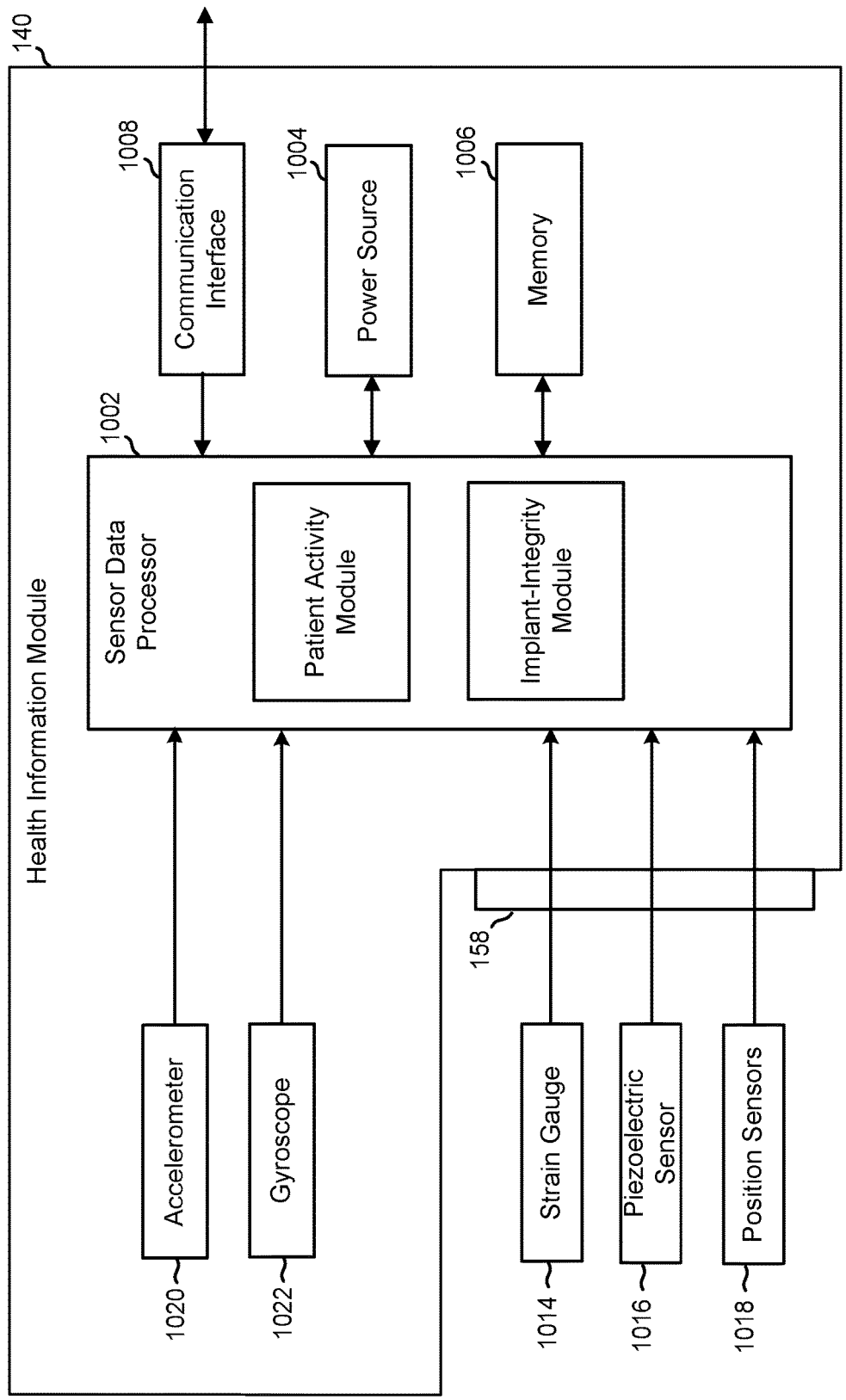
FIG. 10 is a block diagram of the health information module and associated sensors of FIG. 1B.

FIG. 10 is a block diagram of the health information module 140 and various sensors 1014, 1016, 1018, 1020, 1022 that may function as one or both of an implant-integrity sensor and patient health sensors. The sensors include one or more strain gauges 1014, piezoelectric sensors 1016, position sensors 1018, each located remote from the health information module 140, and one or more accelerometers 1020 and gyroscopes 1022, each located within the information module. Sensors remote from the health information module 140 connect to a cable connector 158 or header of the module by cables. The cable connector 158 physically secures the cables to the health information module 140 and physically and electrically couples each sensor to a sensor data processor 1002 within the health information module 140.

The sensor data processor 1002 may obtain and process signals from the sensors 1014, 1016, 1018, 1020, 1022 to determine metrics indicative of the mechanical integrity of the implant device and/or patient heath. Alternatively, or in addition to, the external patient interface device 106 may obtain information from the health information module 140 and process the information to determine metrics. Several device-integrity metrics and patient-health metrics are envisioned, and the system 100 may be configured to determine one or more of these metrics.

A first device-integrity metric, referred to as a "load-bearing" metric, provides an indication of the load distribution among different hardware components of an orthopedic implant device. Most implant devices are configured so that after implant and after sufficient healing, the weight or force of the bone structure (herein referred to as "the load" of the bone structure) being applied to the implant device is distributed among hardware components of the device so that some components bear more of the load than other components. For example, in the spinal fixation device 108b shown in FIG. 1E, the pedicle screws 150a, 150b implanted in bone are intended to carry more load than the rod 152. A load distribution among hardware components that does not compart with the intended distribution may indicate that healing is not complete or that the implant device is not stable relative to the bone. Continuing with the spinal fixation device 108b shown in FIG. 1E, the device may become unstable or loose due to insufficient regrowth or fusion of boney material surrounding the pedicle screws 150a, 150b. In this case, some of the load that would otherwise be carried by the pedicle screws would be redistributed to the rod 152.

A lead-bearing metric may be obtained, for example, through a strain gauge 1014 or piezoelectric sensor 1016 associated with a hardware component of the orthopedic implant device. The output of either of these sensors 1014, 1016 may serve as a measure of load carried by the component to which it is attached. Monitoring the output overtime allows for detection of changes in load that may correlate to reduced device integrity. For example, an increase in strain gauge 1014 output from a component that is not intended to carry as much load as another component indicates that the other component is loose. Again, continuing with the spinal fixation device 108b shown in FIG. 1E, an increase in output of a strain gauge 1014 attached to the rod 152 indicates that the pedicle screws 150a, 150b are loose.

A second device-integrity metric, referred to as a "relative-position" metric, provides an indication of the relative positions of different hardware components of an orthopedic implant device. Most implant devices are configured so that after implant and after sufficient healing, the positions of different hardware components of the device relative to each other are fixed. For example, in the spinal fixation device 108b shown in FIG. 1E, the relative positions of pedicle screws 150a, 150b and the rod 152 should be fixed. A relative position finding or metric among hardware components that does not compart with a fixed positioning may indicate that one or both of the hardware components is not stable. Continuing with the spinal fixation device 108b shown in FIG. 1E, the device may become unstable or loose due to insufficient regrowth or fusion of boney material surrounding the pedicle screws 150a, 150b. In this case, the relative position between the pedicle screws 150a, 150b and rod 152 would change from a baseline value.

A relative position metric may be obtained, for example, through position sensors 1018, such as GPS sensors, that are associated with hardware components of the orthopedic implant device. The output of the position sensors 1018 may serve as a measure of distance between the two components. Monitoring the output overtime allows for detection of changes in distance that may correlate to reduced device integrity. For example, an increase in distance indicates that the hardware components have moved relative to each other. Again, continuing with the spinal fixation device 108b shown in FIG. 1E, an increase in the distance between the rod 152 and either of the pedicle screws 110a, 110b indicates that one of the hardware components has moved and may be loose.

A third device-integrity metric, referred to as a "stability" metric, provides an indication of the stability of one or more hardware components of an orthopedic implant device. Implant devices are configured so that after implant and after sufficient healing, the different hardware components of the device are fixed in place. For example, in the spinal fixation device 108b shown in FIG. 1E, the pedicle screws 150a, 150b and the rod 152 should be fixed. A stability metric for a hardware component that does not compart with that of stable and fixed position may indicate that one or both of the hardware components is loose. Continuing with the spinal fixation device 108b shown in FIG. 1E, the device may become unstable or loose due to insufficient regrowth or fusion of boney material surrounding the pedicle screws 150a, 150b.

A stability metric may be obtained, for example, through an accelerometer 1020 within the health information module 140. The accelerometer 1020 senses motion and vibration and outputs signals representing such movements. Some movements may be due to patient activity, while other movements may be due to movement of a hardware component. For example, a loose pedicle screw 150a, 150b may lead to vibration of the rod 152 which in turn would result in vibration of the health information module 140 secured to the rod. The sensor data processor 1002 within the health information module 140 may process the signals to distinguish between movement due to the patient from movement due to the implant device. This may be done through filtering and spectral analysis of the accelerometer signal, wherein movement resulting from vibration of the rod 152 is at a different spectral frequency component that that caused by patient movement.

A first patient-heath metric, referred to herein as an "activity" metric provides an indication of the movement of the patient. An activity metric may be obtained, for example, through the accelerometer 1020 in the health information module 140. As just noted, the accelerometer 1020 senses motion and vibration and outputs signals representing such movements. Some movements may be due to patient activity, while other movements may be due to movement of a hardware component. The sensor data processor 1002 within the health information module 140 may process the signals to distinguish between movement due to the patient from movement due to the implant device. This may be done through filtering and spectral analysis of the accelerometer signal, wherein movement resulting from vibration of the rod 152 is at a different spectral frequency component that that caused by patient movement.

A second patient-heath metric, referred to herein as a "motion" metric provides an indication of the range of motion of the patient. For example, this metric may indicate a patient's ability to bend over, or turn in a certain direction. A motion metric may be obtained, for example, through a gyroscope 1022 in the health information module 140.

In addition to the various sensors, the health information module 140 includes a power source 1004, a memory circuit 1006 and a communication interface 1008. The power source 1004 supplies the voltages and currents necessary for operation of electronic components of the module, including for example, components of the sensor data processor 1002, the sensors and the communication interface 1008. The power source 1004 may be configured to be recharged through an inductive coupling link like the one described above with reference to the RF module 114. In this case, an RF energy interface (like RF energy interface 115) may be coupled to the health information module 140 and the health information module may include charging circuitry (like charging circuitry 214). The memory circuit 1006 may store information corresponding to a history of sensor outputs and metrics determined by the sensor data processor 1002.

The communications interface 1008 enables RF telemetry communication between the health information module and the external patient interface device 106 through a wireless communication link. The external patient interface device 106 allows for the downloading of information from the memory circuit 1006. Information may also be downloaded from the memory circuit 1006 through the inductive coupling link by inductive telemetry when the interface is not being used for charging purposes.

Physical Configurations of Implantable Medical Devices

Figure 11:
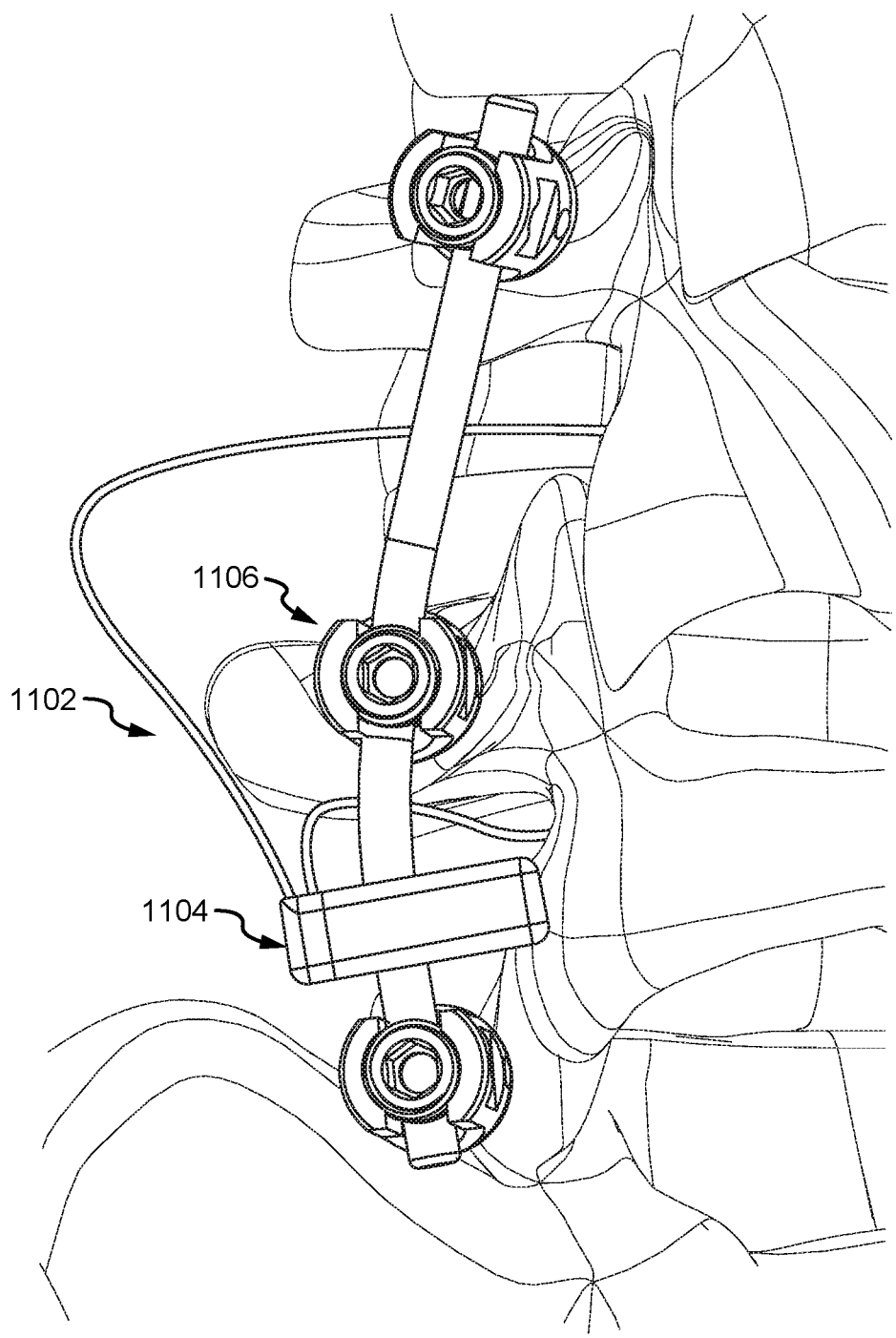
FIG. 11 is an illustration of an alternate arrangement of the implantable medical device of FIG. 1A comprising a RF module coupled to an orthopedic implant device in the form of a spinal fixation device.

Disclosed below, are other embodiments of implantable medical devices having different implant arrangements or different physical configurations than the device of FIG. 1A-1F. In some embodiments, the implantable medical device has a form factor that allows it to be integrated with the overall structure of a spinal fixation device. In another embodiment, components of the implantable medical device are incorporated and integrated into one or more components of the spinal fusion device, e.g. pedicle screw or a rod FIG. 11 is an illustration of an alternate arrangement of an implantable medical device 1102 like that in FIG. 1A comprising a RF module 1104 coupled to an orthopedic implant device 1106 in the form of spinal fixation device. In this arrangement, the RF module 1104 is arrange perpendicular to the rods of the spinal fixation device 1106.

Figure 12A:
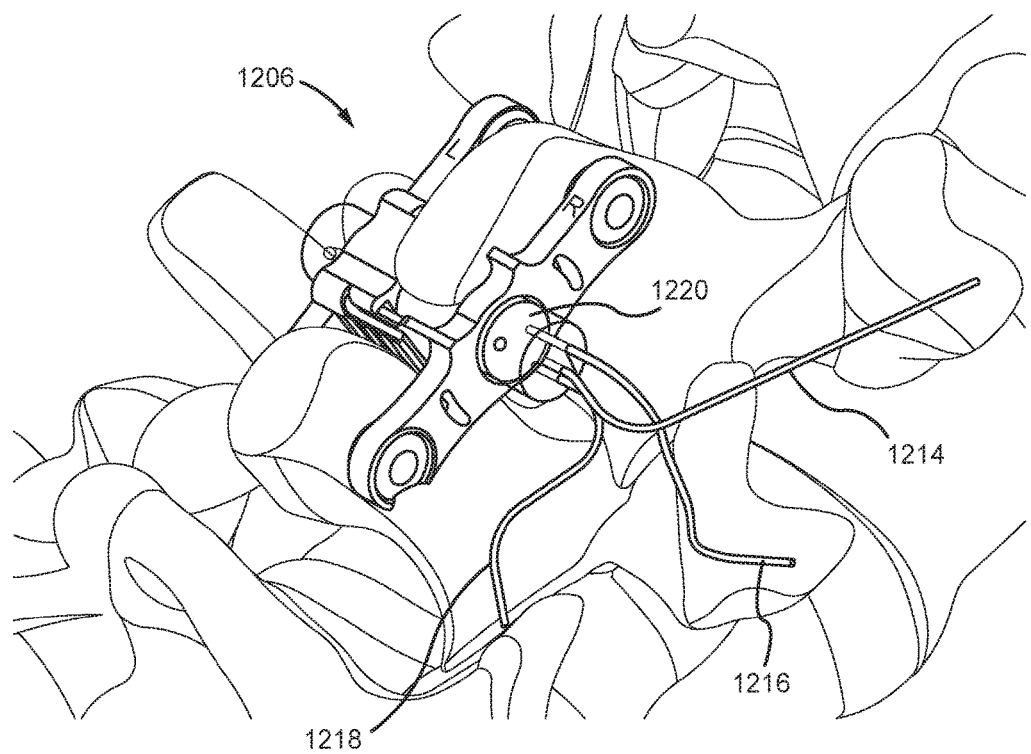
FIGS. 12A, 12B and 12C are illustrations of an embodiment of the implantable medical device of FIG. 1B comprising an RF module configured to fit within a portion of an interspinous process device.
Figure 12B:
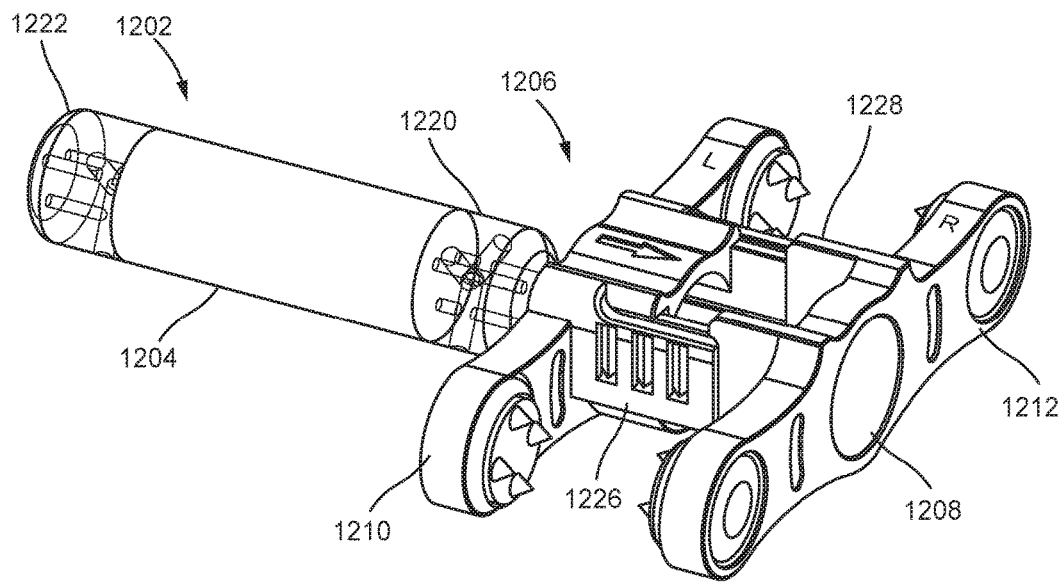
Figure 12C:
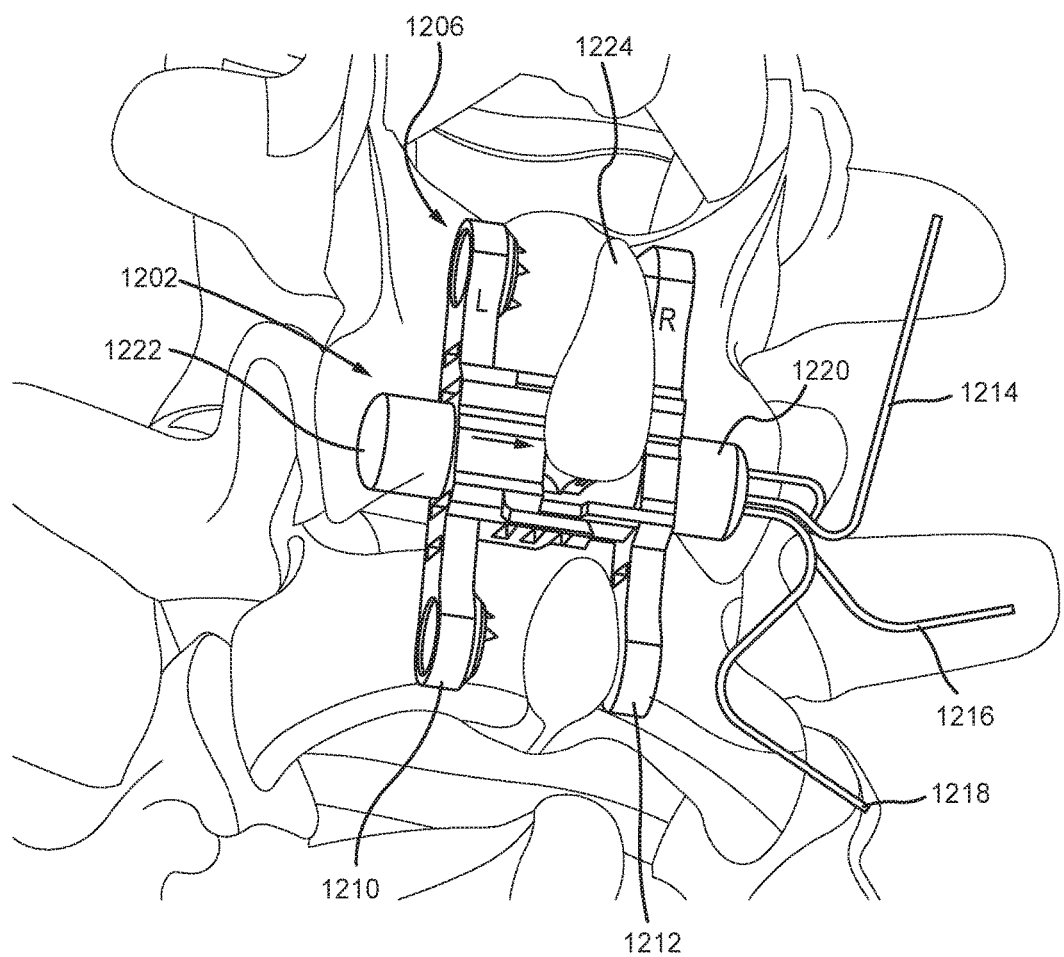

FIGS. 12A, 12B and 12C are illustrations of an RF module 1202 of FIG. 1B, integrated with an orthopedic device in the form of an interspinous process device 1206. The RF module 1202 includes a housing 1204 configured to fit within a portion of the interspinous process device 1206. The housing 1204 is in the form of a tube and has a geometric cross-section, e.g., circular cross-section, sized to fit through a circular opening 1208 or passageway extending through one or more components 1210, 1212, of the interspinous process device 1206. The RF module 1202 may be secured in place through a friction fit between the outer wall of the housing 1204 and the inner wall of the interspinous process device 1206A first set of leads 1214, 1216, 1218 may be coupled to the RF module 1202 through a first header 1220 located at an end of the housing, while a second set of leads (not shown) may be coupled to a second header 1222 at the opposite end of the housing. This configuration of the RF module 1202 provides for the implant of lead in, on or adjacent target nerve tissue, e.g., the DRG, on both sides of the spine.

With reference to FIG. 12C, during an implant procedure, a left-side component 1210 and a right-side component 1212 of the interspinous process device 1206 are placed on their respective sides of a spinous process 1224, with respective ratchet portion 1226, 1228 of the components positioned beneath the process. The components 1210, 1212 are then assembled together by aligning the ratchet portion 1226, 1228 and sliding the components together to engage the ratchets. Upon assembly of the components 1210, 1212, a tubular passageway through the interspinous process device 1206 is formed. The RF module 1202 is then placed in the passageway such that a header 1220, 1222 is located at each end of the interspinous process device 1206. The RF module 1202 may be secured in place within the passageway through a friction fit between the outer wall of the housing 1204 and the inner wall of the interspinous process device 1206. Once the RF module is secured in place, the connector ends of the leads 1214, 1216, 1218 are connected to the header 1220. In some implant procedures, the distal ends of leads 1214, 1216, 1218 may have been surgically implanted prior to implant of the interspinous process device 1206. In other implant procedures, the distal ends of leads 1214, 1216, 1218 may been surgically implanted after the interspinous process device 1206 is implanted.

Figure 13:
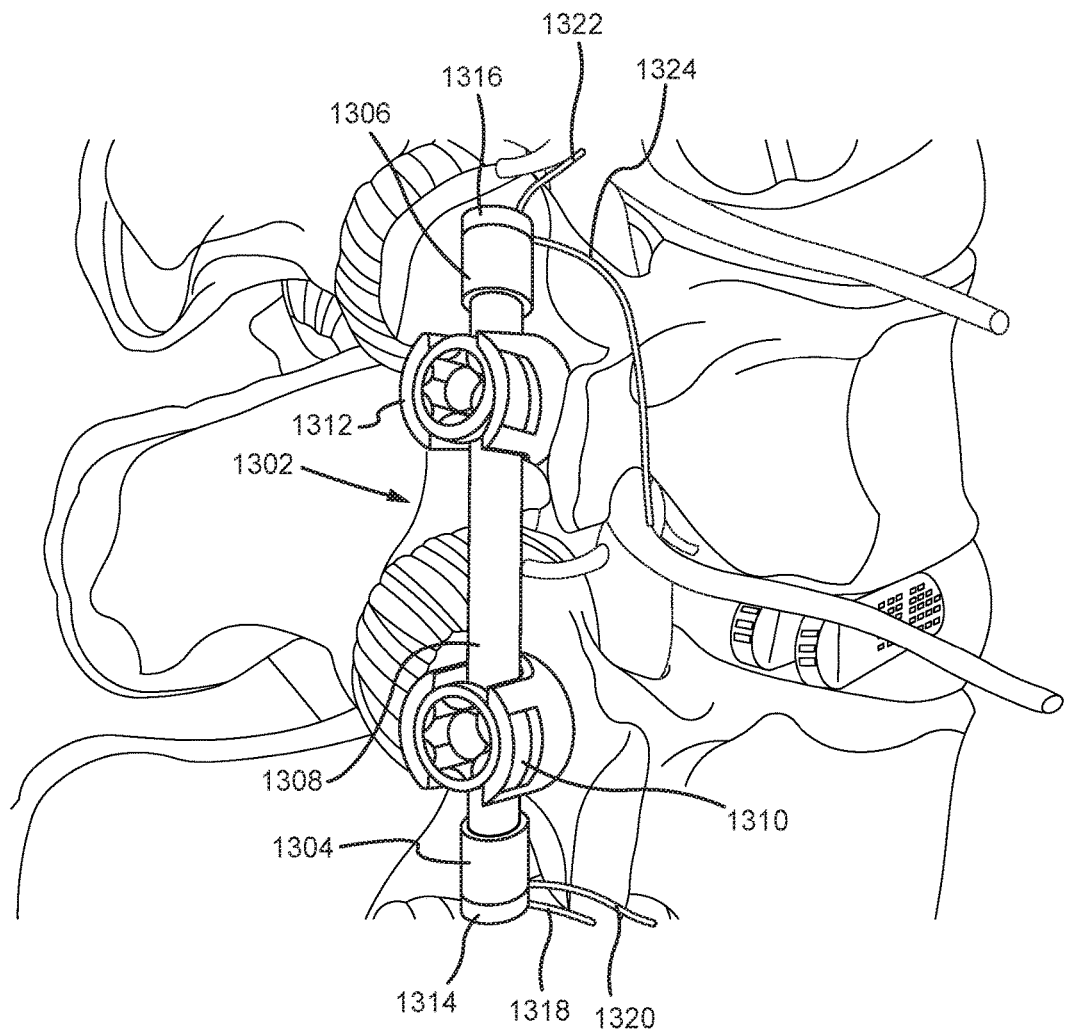
FIG. 13 is an illustration of a spinal fixation device with an integrated RF module.

FIG. 13 is an illustration of a spinal fixation device 1302 with an integrated RF module formed of a pair of electrically interconnected RF module parts 1304, 1306. Integrated in this context means the RF module parts 1304, 1306 are included in the spinal fixation device 1302, and are not separate parts that are attached to the spinal fixation device. In this example embodiment, the spinal fixation device 1302 includes a rod 1308 and a pair of pedicle screws 1310, 1312. Each opposed end of the rod 1308 extending beyond the pedicle screws, includes one of the RF module parts 1304, 1306. Components of the respective RF module parts 1304, 1306 may be electrically coupled by one or more conductors extending through the rod 1308. Configured as such, the RF module parts 1304, 1306 are not included in the load-bearing portion of the rod that extends between the pedicle screws, only the one or more conductors are. As a result, the RF module parts 1304, 1306 will not be subjected to load distribution that may impact the integrity of the components, e.g., energy storage component, RF controller, etc., of the RF module parts. Each RF module part 1304, 1306 includes a header 1314, 1316 that couples with the connector ends of one or more lead 1318, 1320, 1322, 1324.

Figure 14:
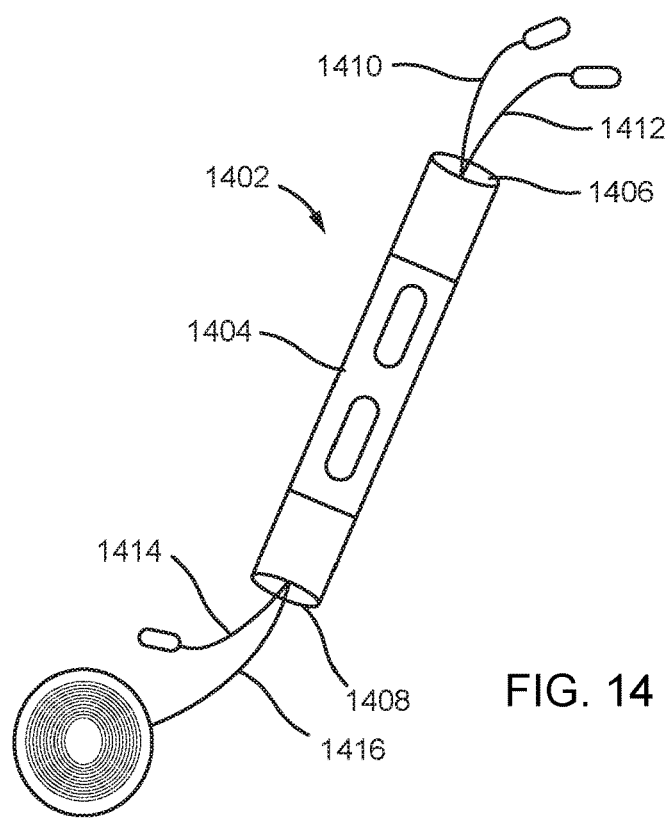
FIG. 14 is a schematic illustration of a rod component of a spinal fixation device with an integrated RF module.

FIG. 14 is a schematic illustration of a component 1402 of a spinal fixation device with an integrated RF module 1404. Integrated in this context means the RF module 1404 is included in the component, and is not a separate part that is attached to the spinal fixation device. The component, in this embodiment, is a rod 1402 of a rod-and-screw spinal fixation device, like the device illustrated in FIG. 1C. The RF module 1404 is housed within the rod 1402. For example, the rod 1402 may be formed as a hollow tube with components of the RF module 1404 placed therein. A header 1406, 1408 is located at each end of the rod 1402 and electrically connects to the RF module 1404 through conductors extending through the rod. The headers 1406, 1408 are located at the ends of the rod 1402 so that after implant of the rod-and-screw spinal fixation device, the headers are positioned on the outer side of the pedicle screws, like described with respect to FIG. 13. The headers 1406, 1408 are configured to connect with one or more leads 1410, 1412, 1414, and an RF energy interface 1416. The RF energy interface 1416 may be configured similar to The RF energy interface 115 shown in FIG. 1A.

Figure 15:
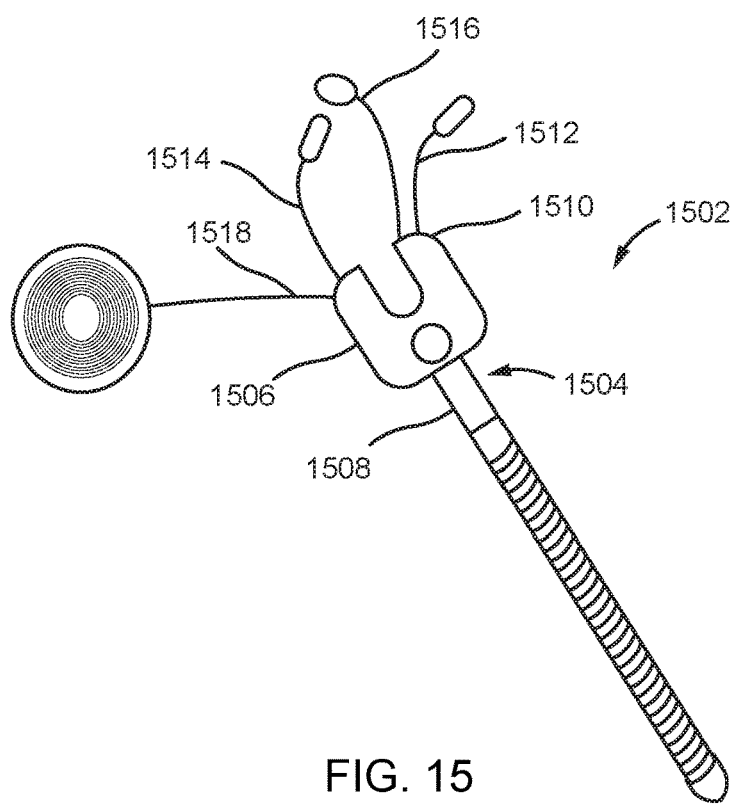
FIG. 15 is a schematic illustration of a pedicle screw component of a spinal fixation device with an integrated RF module.

FIG. 15 is a schematic illustration of a component 1502 of a spinal fixation device with an integrated RF module 1504. Integrated in this context means the RF module 1504 is included in the component, and is not a separate part that is attached to the spinal fixation device. The component, in this embodiment, is a pedicle screw 1502 of a rod-and-screw spinal fixation device, like the device illustrated in FIG. 1C. The RF module 1504 is housed within the screw 1502, with some components of the RF module located in the screw head 1506 and some components located near the top 1508 of the threaded portion of the screw. To this end, the top 1508 of the threaded portion of the screw may be hollowed out with some components of the RF module 1504 placed therein. Likewise, the screw head 1506 may be hollowed out to accommodate other components of the RF module 1504. Components of the RF module 1504 located in the screw head 1506 electrically connect with components in the threaded portion through electrical conductors extending through the screw 1502. A header 1510 is located at the top of the screw head 1506 and electrically connects to the RF module 1504 through conductors extending through the head. The header 1510 is configured to connect with one or more leads 1512, 1514, 1516 and an RF energy interface 1518. The RF energy interface 1518 may be configured similar to The RF energy interface 115 shown in FIG. 1A.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A pain management system, comprising:
   an external device configured to transmit radio frequency (RF) energy through the application of a RF signal to an external RF energy interface, wherein the RF signal oscillates at a frequency in an energy transmission band; and
   an implantable medical device comprising:
   one or more electrodes configured to be implanted in, on, or adjacent a target area of nerves,
   an implantable RF energy interface configured to receive energy from the external RF energy interface over a wireless energy link,
   an energy storage component configured to store the energy, and a RF therapy controller coupled to the energy storage component and the one or more electrodes, the RF therapy controller programmatically configured to:
   1) selectively generate each of three different types of a therapeutic output signal from the stored energy, the three different types of the therapeutic output signal comprising an RF stimulation therapy output signal, an RF heat therapy output signal, and an RF ablation therapy output signal, wherein each of the three different types of the therapeutic output signal comprises an RF signal oscillating at a frequency in a therapy band that is greater than the energy transmission band, and
   2) deliver the therapeutic output signal to the one or more electrodes;
   wherein the RF stimulation therapy output signal comprises pulses of the RF signal configured to generate an alternating current field at or near the target area at a current level sufficient to modulate neural signals by altering or interrupting transmission of action potentials by one or more nerves while maintaining the target area below a first temperature;
   wherein the RF heat therapy output signal comprises pulses of the RF signal or a continuous RF signal configured to generate an alternating current field at or near the target area sufficient to increase the temperature of the target area to a value within a temperature range that is above the first temperature in order to provide analgesic heat to alleviate pain without causing nerve cell necrosis; and
   wherein the RF ablation therapy output signal comprises pulses of the RF signal configured to generate a voltage field at or near the target area sufficient to elevate the temperature at the target area to a value within a temperature range that is above the first temperature to induce necrosis in cells at the target area.

2. The system of claim 1, wherein the energy transmission band is in a range of 40-60 KHz and the therapy band is in a range of 100-600 KHz.

3. The system of claim 1, wherein the external device is configured to transmit continuous RF energy through the application of a continuous RF signal to the external RF energy interface.

4. The system of claim 1, wherein the external device is further configured to transmit RF energy through the application of a RF signal that oscillates at a frequency in a diathermy band less than the therapy band.

5. The system of claim 4, wherein the diathermy band is in a range of 40-60 KHz.

6. The system of claim 1, wherein the therapy band is in a range of 100-600 KHz, and the RF stimulation therapy output signal comprises a pulse train having a pulse frequency between 1 Hz and 10 KHz, a pulse amplitude between 0.3 mA and 20 mA, a pulse width of between 5 µsec and 250 µsec.

7. The system of claim 6, wherein a duration of the RF stimulation therapy output signal is in a range of 20-30 minutes.

8. The system of claim 1, wherein the therapy band is in a range of 100-600 KHz, and the RF ablation therapy output signal comprises a pulse train, having a duty cycle up to 50%, a pulse amplitude between 45V and 60V, and a pulse width of 0.050 msec.

9. The system of claim 8, wherein a duration of the RF ablation therapy output signal is in a range of 140-220 seconds.

10. The system of claim 1, wherein the therapy band is in a range of 100-600 KHz, and the RF heat therapy output signal comprises a pulse train has a duty cycle between 50 and 95%, a single electrode pulse amplitude between 1 mA and 50 mA, a pulse train duration of between continuous and 50% of time.

11. The system of claim 10, wherein the duration of the RF heat therapy output signal is in a range of 20-30 minutes.

12. The system of claim 1, wherein the RF therapy controller comprises:
    an RF modality controller;
    an RF signal generator; and
    an energy supply controller configured to receive a control signal from the RF modality controller and to, based on the control signal, output energy to the RF signal generator at an energy level and in an on/off cycle pattern than defines one or more parameters of a selected one of the three different types of the therapeutic output signal.

13. The pain management system of claim 1, wherein the implantable medical device comprises a housing configured to enclose the RF therapy controller, and to be mechanically coupled to a hardware component of an orthopedic implant device.

14. The pain management system of claim 1, wherein the controller is configured to selectively generate the three different types of a therapeutic output signal in series in the following order: RF stimulation therapy output signal, followed by either of RF heat therapy output signal and RF ablation therapy output signal.

15. The pain management system of claim 1, wherein the controller is configured to simultaneously generate at least two different types of therapeutic output signals, and deliver a first of the different types therapeutic output signals to a first pair of electrodes and a second of the different types therapeutic output signals to a second pair of electrodes.

16. An implantable medical device configured for chronic implant, the device comprising:
    one or more electrodes configured to be implanted in, on, or adjacent a target area of nerves;
    an RF energy interface configured to receive energy from an external RF energy interface over a wireless energy link;
    an energy storage component coupled to the RF energy interface through charging circuitry and configured to store the energy; and a RF therapy controller coupled to the energy storage component and the one or more electrodes, the RF therapy controller programmatically configured to:
1) selectively generate each of three different types of a therapeutic output signal from the stored energy, the three different types of the therapeutic output signal comprising an RF stimulation therapy output signal, an RF heat therapy output signal, and an RF ablation therapy output signal, wherein each of the three different types of the therapeutic output signal comprises an RF signal oscillating at a frequency in a therapy band, and
2) deliver the therapeutic output signal to the one or more electrodes;
wherein the RF stimulation therapy output signal comprises pulses of the RF signal configured to generate an alternating current field at or near the target area at a current level sufficient to modulate neural signals by altering or interrupting transmission of action potentials by one or more nerves while maintaining the target area below a first temperature;
wherein the RF heat therapy output signal comprises pulses of the RF signal or a continuous RF signal configured to generate an alternating current field at or near the target area sufficient to increase the temperature of the target area to a value within a temperature range that is above the first temperature in order to provide analgesic heat to alleviate pain without causing nerve cell necrosis; and
wherein the RF ablation therapy output signal comprises pulses of the RF signal configured to generate a voltage field at or near the target area sufficient to elevate the temperature at the target area to a value within a temperature range that is above the first temperature to induce necrosis in cells at the target area.

17. The device of claim 16, wherein the therapy band is in a range of 100-600 KHz.

18. The device of claim 16, wherein the RF stimulation output comprises a pulse train having a pulse frequency between 1 Hz and 10 KHz, a pulse amplitude between 0.3 mA and 20 mA, a pulse width of between 5 μsec and 250 μsec.

19. The device of claim 16, wherein the RF heat output comprises a pulse train has a duty cycle between 50 and 95%, a single electrode pulse amplitude between 1 mA and 50 mA, a pulse train duration of between continuous and 50% of time.

20. The device of claim 16, wherein the RF ablation output comprises a pulse train, having a duty cycle up to 50%, a pulse amplitude between 45V and 60V, and a pulse width of 0.050 msec.

21. A method of delivering radio frequency (RF) therapy to a patient, comprising:
transmitting RF energy through the application of a RF signal to an external RF energy interface, wherein the RF signal oscillates at a frequency in an energy transmission band;
receiving the RF energy at an RF energy interface of an implanted medical device;
storing energy derived from the received RF energy in a direct current (DC) energy storage component of the implanted medical device;
generating, at an RF therapy controller of the implanted medical device, a selected one of three different types of a therapeutic output signal from the stored energy, the three different types of the therapeutic output signal comprising an RF stimulation therapy output signal, an RF heat therapy output signal, and an RF ablation therapy output signal, wherein each of the three different types of the therapeutic output signal comprises an RF signal oscillating at a frequency in a therapy band that is greater than the energy transmission band; and
delivering the therapeutic output signal to one or more electrodes implanted in, on, or adjacent a target area of nerves;
wherein the RF therapy controller is programmatically configured to:
selectively generate each of the RF stimulation therapy output signal, the RF heat therapy output signal, and the RF ablation therapy output signal:
wherein the RF stimulation therapy output signal comprises pulses of the RF signal configured to generate an alternating current field at or near the target area at a current level sufficient to modulate neural signals by altering or interrupting transmission of action potentials by one or more nerves while maintaining the target area below a first temperature;
wherein the RF heat therapy output signal comprises pulses of the RF signal or a continuous RF signal configured to generate an alternating current field at or near the target area sufficient to increase the temperature of the target area to a value within a temperature range that is above the first temperature in order to provide analgesic heat to alleviate pain without causing nerve cell necrosis; and
wherein the RF ablation therapy output signal comprises pulses of the RF signal configured to generate a voltage field at or near the target area sufficient to elevate the temperature at the target area to a value within a temperature range that is above the first temperature to induce necrosis in cells at the target area.

22. The method of claim 21, wherein the RF energy interface and the DC energy storage component are configured to continue to receive RF energy from the external RF energy interface and store the RF energy while the RF therapy controller generates a selected one of the three different types of a therapeutic output signal.

23. The method of claim 21, wherein the energy transmission band is in a range of 40-60 KHz and the therapy band is in a range of 100-600 KHz.

24. The method of claim 21, wherein the energy is transmitted through the application of a continuous RF signal to the external RF energy interface.

25. The method of claim 21, further comprising selecting RF stimulation therapy output for generation and delivery, and subsequent to the delivery of RF stimulation therapy output, selecting RF ablation therapy output for generation and delivery.

26. The method of claim 21, wherein the one or more of the electrodes are located in, on or adjacent a target area of nerves.

27. The method of claim 26, wherein the target area of nerves comprises a dorsal root ganglion (DRG).

* * * * *